(12) United States Patent
Maycock et al.

(10) Patent No.: US 11,708,387 B2
(45) Date of Patent: Jul. 25, 2023

(54) HEXOSE DERIVATIVES, PREPARATION AND USES THEREOF

(71) Applicants: Faculdade de Ciências da Universidade de Lisboa, Lisbon (PT); Instituto De Tecnologia Química E Biológica António Xavier, Oeiras (PT)

(72) Inventors: Christopher David Maycock, Carcavelos (PT); Maria Rita Mendes Bordalo Ventura Centeno Lima, Lisbon (PT); Eva Correia Lourenço, Lisbon (PT); Maria Helena Dias Dos Santos, Carcavelos (PT); Ana Sofia Da Cunha Miguel, Alverca (PT)

(73) Assignees: Faculdade de Ciências da Universidade de Lisboa, Lisbon (PT); Instituto De Tecnologia Química E Biológica António Xavier, Oeiras (PT)

( * ) Notice: Subject to any disclaimer, the term of this patent is extended or adjusted under 35 U.S.C. 154(b) by 0 days.

(21) Appl. No.: 15/125,522

(22) PCT Filed: Mar. 13, 2015

(86) PCT No.: PCT/PT2015/050001
§ 371 (c)(1),
(2) Date: Sep. 12, 2016

(87) PCT Pub. No.: WO2015/137838
PCT Pub. Date: Sep. 17, 2015

(65) Prior Publication Data
US 2018/0170955 A1    Jun. 21, 2018

Related U.S. Application Data

(60) Provisional application No. 61/953,392, filed on Mar. 14, 2014.

(51) Int. Cl.
*C07H 15/04* (2006.01)
*C07H 9/06* (2006.01)

(52) U.S. Cl.
CPC ............... *C07H 15/04* (2013.01); *C07H 9/06* (2013.01)

(58) Field of Classification Search
CPC .................................. C07H 15/04; C07H 9/06
See application file for complete search history.

(56) References Cited

U.S. PATENT DOCUMENTS 9,695,461 B2 * 7/2017 Siegert ..................... C12N 9/54
2013/0143787 A1    6/2013 Siegert et al.

FOREIGN PATENT DOCUMENTS

JP    2020-097767    6/2020
RU    2008126716 A    1/2010
WO    WO 2007/075253 A2    7/2007
WO    WO 2007/097652 A2    8/2007
WO    WO 2012/019844 A2    2/2012

OTHER PUBLICATIONS

Arora et al., FEBS Letters, 2004, 564, p. 121-125. (Year: 2004).*
Lourenco et al., Carb. Res., 2011, 346, p. 163-168. (Year: 2011).*
Sola-Penna et al., Eur. J. Biochem., 248, 1997, p. 24-29. (Year: 1997).*
International Search Report dated Jan. 7, 2015 by the European Patent Office as International Searching Authority in connection with PCT International Application No. PCT/PT2015/050001.
Written Opinion of the International Searching Authority dated Jan. 7, 2015 in connection with PCT International Application No. PCT/PT2015/050001.
Reply to the Written Opinion of the International Searching Authority, filed on Jan. 14, 2016 in connection with PCT International Application No. PCT/PT2015/050001.
Second Written Opinion of the International Searching Authority dated Feb. 15, 2016 in connection with PCT International Application No. PCT/PT2015/050001.
International Preliminary Report on Patentability dated Jul. 4, 2016 in connection with PCT International Application No. PCT/PT2015/050001.

(Continued)

*Primary Examiner* — Jonathan S Lau
(74) *Attorney, Agent, or Firm* — Gary J. Gershik

(57) ABSTRACT

A compound of formula I:

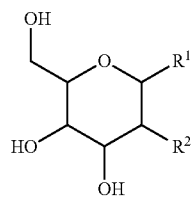

Formula I or a salt thereof, wherein:
$R^1$ is —OC(H)(X)(CH$_2$)$_n$C(=O)OH;
$R^2$ is —OH, —N$_3$, or —N(H)C(=O)CH$_3$; or
$R^1$ and $R^2$ together with the carbon atoms to which they are attached form

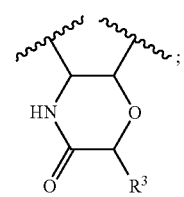

$R^3$ is —H, —CH$_3$, —CH$_2$C(=O)OH, or —CH$_2$OH;
X is —H, —CH$_3$, —CH$_2$OH, or CH$_2$C(=O)OH; and
n is 0 or 1.

16 Claims, 6 Drawing Sheets

(56) References Cited

OTHER PUBLICATIONS

Khodair et al. "A Convenient Route to O-Glycosyl Lactates via Conjugate Addition to 2-Nitro-glycals: Ring Closure to Novel Pyrano [2.3-b] [1,4]-oxazines" Synthesis, vol. 2004, No. 1, Jan. 1, 2004, pp. 53-58.

Ascencio et al. "Complete $^1$H and $^{13}$C NMR assignment of digeneaside, a low-molecular-mass carbohydrate produced by red seaweeds", Carbohydrate Research, Pergamon, GB, vol. 341, No. 5, Apr. 10, 2006 (Apr. 10, 2006), pp. 677-682.

Rotzoll et al. "Activity-Guided Identification of (S)-Malic Acid 1-O-D-Glucopyranoside (Morelid) and γ-Aminobutyric Acid as Contributors to Umami Taste and Mouth-Drying Oral Sensation of Morel Mushrooms (*Moichella deliciosa* Fr.)" Journal of Agricultural and Food Chemistry, vol. 53, No. 10, Jan. 1, 2005 (Jan. 1, 2005), pp. 4149-4156.

Hermansson et al. "Isolation and Characterization of 2-0-Beta-D-Glucopyranosyl-L-Malic Acid From Synadenium Pereskiifolium", Phytochemistry, vol. 29, No. 2, Jan. 1, 1990 (Jan. 1, 1990), pp. 513-515.

Sawangwan T et al. "Single-step enzymatic synthesis of (R)-2-0-alpha-D-glycopyranosyl glycerate, a compatible solute from microorganisms that functions as a protein stabiliser," Organic & Biomolecular Chemistry, Royal Society of Chemistry, vol. 7, Jan. 1, 2009 (Jan. 1, 2009), pp. 4267-4270, [retrieved on Aug. 12, 2009].

Shimoda et al. Chemo-enzymatic synthesis of ester-linked taxol-oligosaccharide conjugates as potential prodrugs, Tetrahedron Letters, Pergamon, GB, vol. 49, No. 4, Dec. 3, 2007 (Dec. 3, 2007), pp. 601-604.

Timell, "The Acid Hydrolysis of Glycosides: I. General Conditions and the Effect of the Nature of the Aglycone", Canadian Journal of Chemistry, vol. 42, No. 6, Jun. 1, 1964 (Jun. 1, 1964), pp. 1456-1472.

Listkowski et al. "Carboxymethylglycoside lactones (CMGLs) : structural variations on the carbohydrate moiety," Tetrahedron Asymmetry, vol. 18, No. 18, Oct. 12, 2007 (Oct. 12, 2007), pp. 2201-2210.

Sharma et al. "Chemical and Chemoenzymatic Syntheses of Bacillithiol: a Unique Low-Molecular-Weight Thiol amongst Low Gram-Positive Bacteria", Angewandte Chemie International Edition, vol. 50, No. 31, Jul. 25, 2011 (Jul. 25, 2011), pp. 7101-7104.

Stortz et al. "Polysaccharides from Peptostreptococcus anaerobius and structure of the species-specific antigen," Carbohydrate Research, vol. 207, No. 1, Oct. 1, 1990 (Oct. 1, 1990), pp. 101-120.

Tomabechi et al. "Chemo-enzymatic synthesis of glycosylated insulin using a GlcNAc tag", Bioorganic & Medicinal Chemistry, vol. 18, No. 3, Feb. 1, 2010 (Feb. 1, 2010), pp. 1259-1264.

Katsuhiko Suzuki et al. "Synthesis of 3-O-β-D-Glucopyranosyl-(3R)-hydroxybutanolide (Kinsenoside) and 3-O-β-D-Glucopyranosyl-(3S)-hydroxybutanolide (Goodyeroside A)," Journal of Carbohydrate Chemistry, vol. 24, No. 1, Jan. 1, 2005 (Jan. 1, 2005), pp. 73-84.

Faria et al. "Design of new enzyme stabilizers inspired by glycosides of hyperthermophilic microorganisms," Carbohydrate Research, vol. 343, No. 18, Dec. 8, 2008 (Dec. 8, 2008), pp. 3025-3033.

Jul. 16, 2018 Office Action, issued in connection with Chinese Patent Application No. 2015800143864, including English language translation.

Nov. 30, 2018 Response to Jul. 16, 2018 Office Action, issued in connection with Chinese Patent Application No. 2015800143864.

Oct. 30, 2018 Office Action issued by the Patent Office of the Russian Federation in connection with Russian Patent Application No. 2016140337, including English language translation.

Feb. 25, 2019 Communication pursuant to Article 94 (3) EPC issued by the European Patent Office in connection with European Application No. 15724386.6.

Brazilian Office Action dated Oct. 15, 2019 in connection with Brazilian Patent Application No. 1120160212312 including English summary provided by Foreign Agent.

Chinese Office Action dated Mar. 21, 2019 in connection with Chinese Patent Application No. 201580014386.4 including English summary provided by Foreign Agent.

Chinese Office Action dated Sep. 30, 2019 in connection with Chinese Patent Application No. 201580014386.4 including English summary provided by Foreign Agent.

Mexican Office Action dated Oct. 22, 2019 in connection with Mexican Patent Application No. MX/a/2016011808 including English summary provided by Foreign Agent.

Israeli Office Action dated Jun. 2, 2019 in connection with Israeli Patent Application No. 247531 including English summary provided by Foreign Agent .

Russian Office Action dated Oct. 25, 2019 in connection with Russian Patent Application No. 2016140337 including English summary provided by Foreign Agent.

Indian Office Action dated May 21, 2019 in connection with Indian Patent Application No. 201617034596 including English summary provided by Foreign Agent.

Aug. 5, 2019 Response to Feb. 25, 2019 Communication pursuant to Article 94 (3) EPC issued by the European Patent Office in connection with European Patent Application No. 15724386.6.

English language translation of Japanese Office Action dated Feb. 4, 2020 in connection with Japanese Patent Application No. 2016-575290.

Israeli Office Action dated Feb. 13, 2020 in connection with Israeli Patent Application No. 247531 including English translation provided by the Patent Office of the State of Israel.

Feb. 20, 2020 Response to May 21, 2019 Office Action in connection with Indian Patent Application No. 201617034596.

English language translation of Chinese Office Action dated Apr. 17, 2020 in connection with Chinese Patent Application No. 201580014386. 4, provided by China National Intellectual Property Administration, PRC.

Notice of Allowance dated May 18, 2021 in connection with Brazilian Patent Application No. 1120160212312 including English language translation provided by Foreign Agent.

Office Action dated Apr. 7, 2021 in connection with Canadian Patent Application No. 2,942,635.

Amendment filed Jul. 30, 2021 with the Canadian Intellectual Property Office (CIPO) in connection with Canadian Patent Application 2,942,635.

Office Action dated Oct. 14, 2021 in connection with Canadian Patent Application 2,942,635.

Office Action dated Jan. 5, 2022 in connection with Chinese Patent Application No. 2015800143864 including English language translation provided by Foreign Agent.

Office Action dated Aug. 6, 2020 in connection with European Patent Application No. 15724386.6.

Response filed Feb. 16, 2021 with the European Patent Office in connection with European Patent Application No. 15724386.6.

Amendment filed Aug. 13, 2020 with the Israeli Patent Office in connection with Israeli Patent Application No. 247531.

Office Action dated Aug. 20, 2020 in connection with Israeli Patent Application No. 247531 including English language summary provided by Foreign Agent.

Amendment filed Dec. 27, 2020 with the Israeli Patent Office in connection with Israeli Patent Application No. 247531 including informal English language version.

Notice of Allowance dated Jan. 17, 2021 in connection with Israeli Patent Application No. 247531 including English language summary provided by Foreign Agent.

Official Notice of termination of the pre-appeal examination dated Sep. 1, 2020 and Pre-appeal Examination Report in connection with Japanese Patent Application No. 2016-575290 including English language translation provided by Foreign Agent.

Written Statement in response to Pre-appeal Examination Report filed Dec. 25, 2020 in connection with Japanese Patent Application No. 2016-575290 including informal English language version.

Office Action dated Aug. 17, 2021 in connection with Japanese Patent Application No. 2016-575290 including English language translation provided by Foreign Agent.

(56) References Cited

OTHER PUBLICATIONS

Office Action dated Jun. 15, 2021 in connection with Japanese Patent Application No. 2020-097767 including English language translation provided by Foreign Agent.
Amendment filed Dec. 15, 2021 with the Japan Patent Office in connection with Japanese Patent Application No. 2020-097767 including informal English language version.
Office Action dated Apr. 21, 2021 in connection with Korean Patent Application No. 10-2016-7028609 including English language translation provided by Foreign Agent.
Amendment filed Oct. 21, 2021 with the Korean Intellectual Property Office in connection with Korean Patent Application No. 10-2016-7028609 including informal English language version.
Amendment filed Feb. 24, 2020 with the Mexican Patent Office in connection with Mexican Patent Application No. MX/a/2016/011808 including informal English language version.
Office Action dated Aug. 6, 2020 in connection with Mexican Patent Application No. MX/a/2016/011808 including English language translation provided by Foreign Agent.
Amendment filed Dec. 4, 2020 with the Mexican Patent Office in connection with Mexican Patent Application No. MX/a/2016/011808 including informal English language version.
Office Action dated Mar. 9, 2021 in connection with Mexican Patent Application No. MX/a/2016/011808 including English language translation provided by Foreign Agent.
Amendment filed Jul. 9, 2021 with the Mexican Patent Office in connection with Mexican Patent Application No. MX/a/2016/011808 including informal English language version.
Decision of Grant dated Jul. 6, 2020 in connection with Russian Patent Application No. 2016140337 including English language translation provided by Foreign Agent.

\* cited by examiner

HEXOSE DERIVATIVES, PREPARATION AND USES THEREOF

This application claims the priority of U.S. Provisional Application No. 61/953,392, filed Mar. 14, 2014, the contents of which are hereby incorporated by reference.

Throughout this application, various publications are referenced, including referenced in parenthesis. Full citations for publications referenced in parenthesis may be found listed in alphabetical order at the end of the specification immediately preceding the claims. The disclosures of all referenced publications in their entireties are hereby incorporated by reference into this application in order to more fully describe the state of the art to which this invention pertains.

BACKGROUND OF THE INVENTION

Low molecular weight organic compounds termed compatible solutes have been identified in the cytoplasm of many halophilic or halotolerant organisms which counterbalance the osmotic pressure of the external medium and which promote correct protein folding, inhibit protein aggregation, and prevent heat-induced denaturation (Faria 2008, Faria 2013). Compatible solutes are therefore industrially useful, for example, for stabilizing proteins in pharmaceutical and cosmetic formulations (Luley-Goedl 2011, Lentzen 2006).

Compatible solutes are usually amino acids, carbohydrates, polyols, betaines and ectoines. Trehalose, glycerol, glycine-betaine and ectoine are typical compatible solutes of mesophiles. The discovery of extreme thermophilic and hyperthermophilic microorganisms led to the discovery of additional compatible solutes, such as mannosylglycerate (MG) and dimyo-inositol-1,3'-phosphate (Faria 2008).

Compounds structurally related to MG, namely (2S)-2-(1-O-α-D-Mannopyranosyl)propionate (ML), 2-(1-O-α-Dmannopyranosyl) acetate (MGlyc), 1-O-(2-glyceryl)-α-D-mannopyranoside (MGOH), have been synthesized and tested for their ability to stabilize model proteins against thermal stress. (Faria 2008).

New compounds for the stabilization of biological materials are needed.

SUMMARY OF THE INVENTION

The invention provides a compound of formula I:

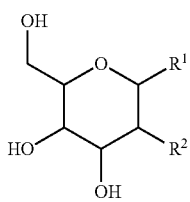

Formula I or a salt thereof, wherein:

$R^1$ is —OC(H)(X)(CH$_2$)$_n$C(=O)OH;

$R^2$ is —OH, —N$_3$, or —N(H)C(=O)CH$_3$; or $R^1$ and $R^2$ together with the carbon atoms to which they are attached form

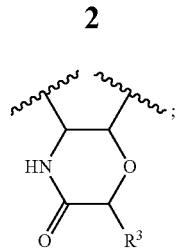

$R^3$ is —H, —CH$_3$, —CH$_2$C(=O)OH, or —CH$_2$OH;

X is —H, —CH$_3$, —CH$_2$OH, or CH$_2$C(=O)OH; and n is 0 or 1;

wherein when the compound is

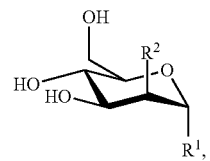

and $R^2$ is OH, X is CH$_3$, and n is 0, then the compound is

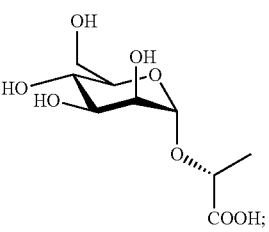

wherein when the compound is

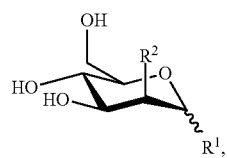

and $R^2$ is OH, X is H, and n is 0, then the compound is

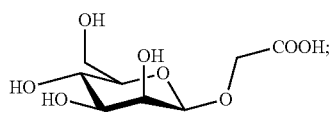

wherein when the compound is

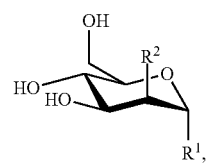

and $R^2$ is OH, X is $CH_2OH$, and n is 0, then the compound is

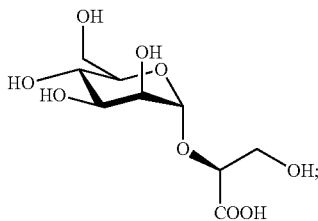

and wherein when the compound is

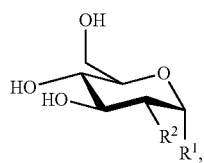

and $R^2$ is OH, X is $CH_2OH$, and n is 0, then the compound is

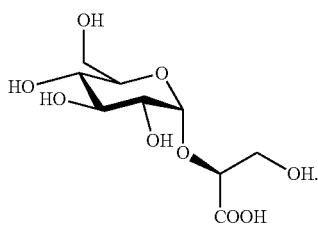

The invention further provides a composition comprising at least one compound of Formula I, or a salt thereof, and a biological material.

The invention further provides a method of stabilizing a biological material, comprising adding at least one compound of Formula I, or a salt thereof, to a solution containing the biological material to form a stabilized solution.

The invention further provides a compound of Formula I or a salt thereof, for stabilizing a biological material.

The invention further provides a use of the compound of Formula I, or a salt thereof, for stabilizing a biological material.

DETAILED DESCRIPTION OF THE INVENTION

Figure 1:
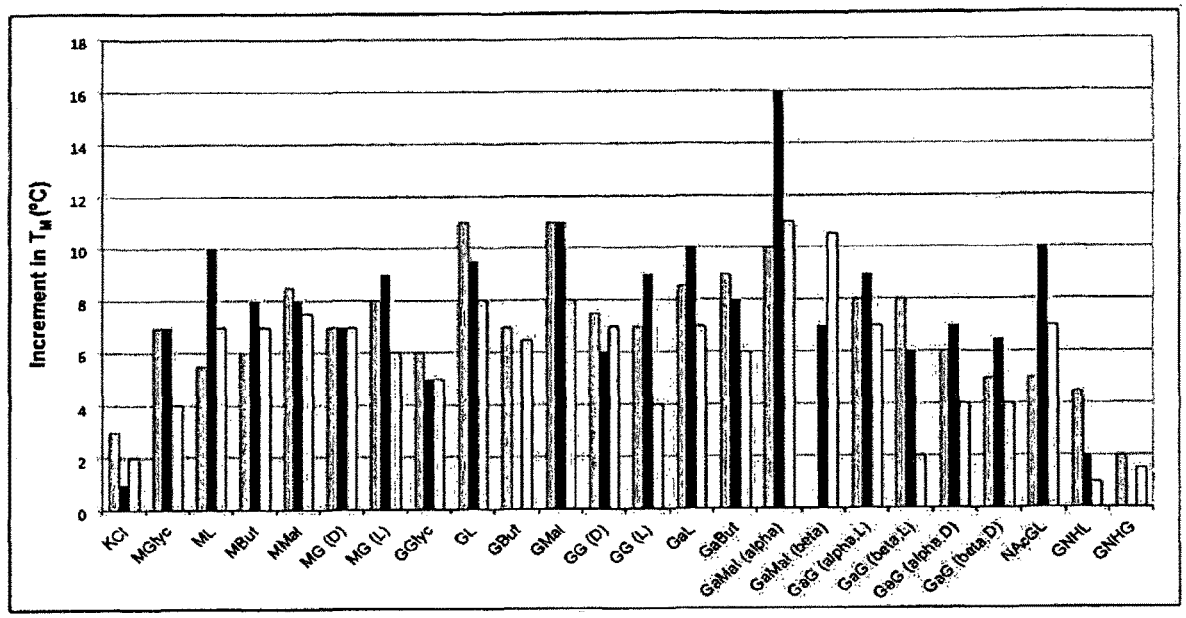
FIG. 1: Increment in the melting temperature (TM) of malate dehydrogenase (MDH, grey bars), staphylococcal nuclease (SNase, black bars) and lysozyme (white bars) in the presence of 0.5 M of different solutes. The melting temperatures ($T_M$) in the absence of solutes were 50° C. for MDH, 52° C. for SNase and 71° C. for lysozyme.

The following abbreviations are used throughout this application.
Ac Acetate
BnBr Benzyl bromide
DIP di-myo-inositol phosphate
DGP di-Glycerol phosphate
DMAP 4-Dimethylaminopyridine
DMF Dimethylformamide
DSF Differential Scanning Fluorimetry
Et Ethyl
$Et_2O$ Diethyl ether
EtOAc Ethyl acetate
GG α-D-Glucosyl-D-glycerate
GGG α-D-glucopyranosyl-(1→6)-α-D-glucopyranosyl-(1→2)-D-glycerate
GL α-D-Glucosyl-S-lactate
Hex Hexane
MDH Malate dehydrogenase Me Methyl
MeOH Methanol
MG α-D-Mannosyl-D-glycerate
MGA α-D-Mannosyl-D-glyceramide
MGG α-D-Mannopyranosyl-(1→2)-α-D-glucopyranosyl-(1→2)-D-glycerate
MGly α-D-Mannosyl-glycolate
MGGly (2R)-2-(1-O-α-D-mannopyranosyl)-3-(1-O-α-D-glucopyranosyl)-glycerate
ML α-D-Mannosyl-S-lactate
NaOMe Sodium methoxide
NIS N-Iodosuccinimide
NMR Nuclear magnetic resonance
Ph Phenyl
TLC Thin layer chromatography
SNase Staphylococcal nuclease
TBAF Tetra-n-butylammonium fluoride
TBDPSCl tert-Butylchlorodiphenylsilane
TBDMS tert-Butyldimethylsilane
TfOH Trifluoromethanesulfonic acid
THF Tetrahydrofuran The invention provides a compound of formula I:

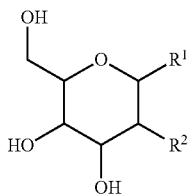

Formula I or a salt thereof, wherein:
R¹ is —OC(H)(X)(CH₂)ₙC(=O)OH;
R² is —OH, —N₃, or —N(H)C(=O)CH₃; or
R¹ and R² together with the carbon atoms to which they are attached form

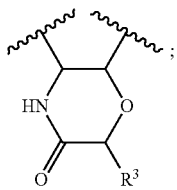

;

R³ is —H, —CH₃, —CH₂C(=O)OH, or —CH₂OH;
X is —H, —CH₃, —CH₂OH, or CH₂C(=O)OH; and
n is 0 or 1;
wherein when the compound is

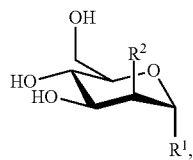

and R² is OH, X is CH₃, and n is 0, then the compound is

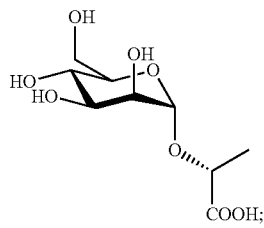

wherein when the compound is

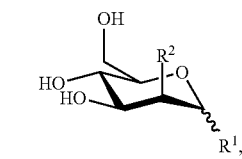

and R² is OH, X is H, and n is 0, then the compound is

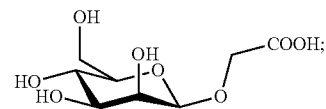

wherein when the compound is

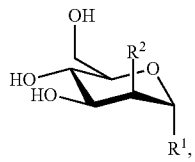

and R² is OH, X is CH₂OH, and n is 0, then the compound is

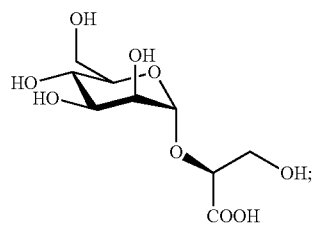

and wherein when the compound is

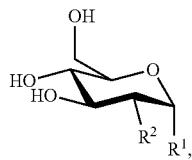

and $R^2$ is OH, X is $CH_2OH$, and n is 0, then the compound is

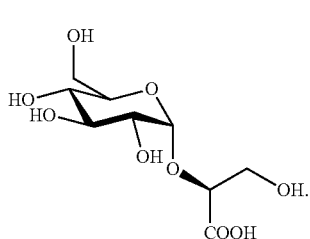

In an embodiment, the compound is not

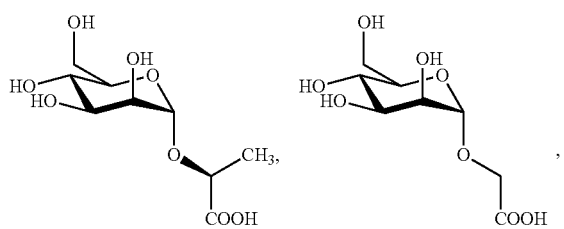

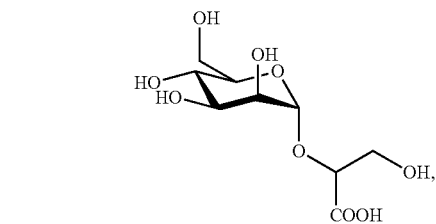

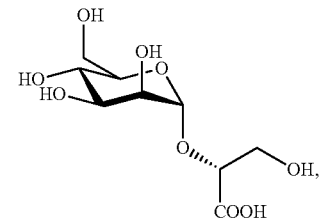

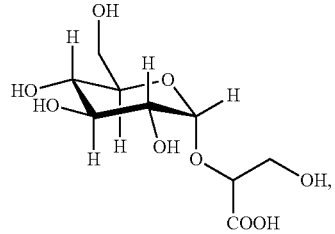

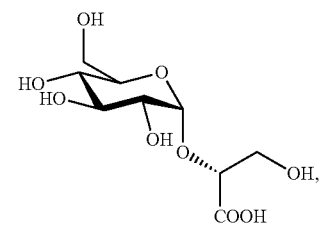

a salt thereof.

In an embodiment, the compound of formula I is not a naturally occurring compound.

In an embodiment, the compound is

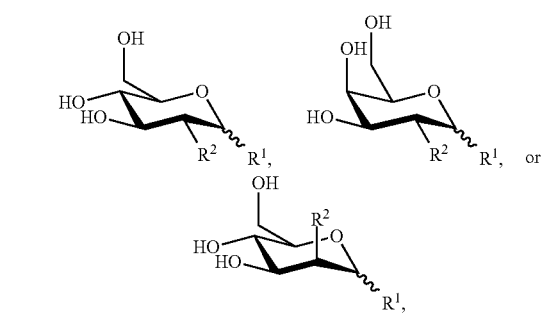

or a salt thereof.

In an embodiment, the compound is

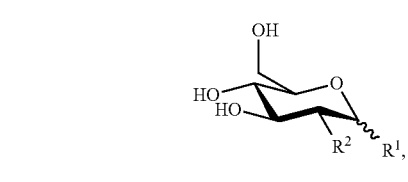

or a salt thereof.

In an embodiment, the compound is

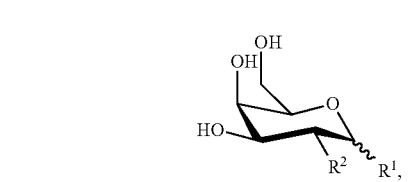

or a salt thereof.

In an embodiment, the compound is

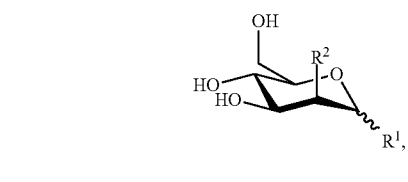

or a salt thereof.

In an embodiment, the α/β anomer ratio of the compound or a salt thereof is 1:1 to 99:1. In an embodiment, the α/β anomer ratio of the compound or a salt thereof is 1:1 to 10:1. In an embodiment, the α/β anomer ratio of the compound or a salt thereof is 1:1 to 5:1. In another embodiment, α/β anomer ratio of the compound or a salt thereof is 1:1, 2:1, 3:1, 4:1, 5:1, 6:1, 7:1, 8:1, 9:1, or 10:1. In an embodiment, the α/β anomer ratio of the compound or a salt thereof is greater than 10:1. In an embodiment, α/β anomer ratio of the compound or salt thereof is greater than 99:1. In an embodiment, the compound or salt thereof is the α anomer.

In an embodiment, $R^1$ is

-continued
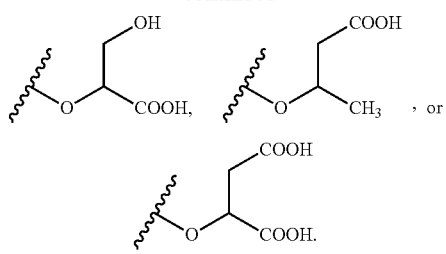
In an embodiment, $R^1$ is
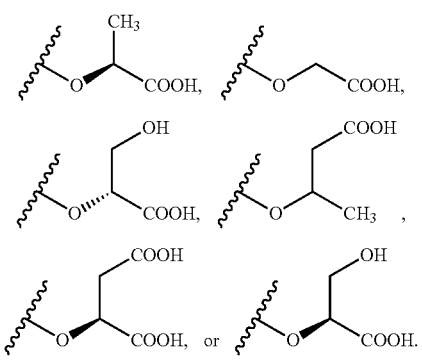
In an embodiment, $R^1$ is
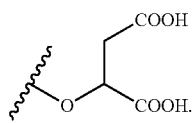
In an embodiment, $R^1$ is
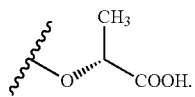
In an embodiment, $R^1$ is
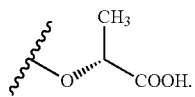
In an embodiment, $R^1$ is
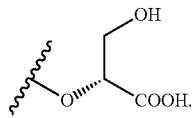 [SMILES: *O[C@H](CO)C(=O)O]
In an embodiment, $R^1$ is
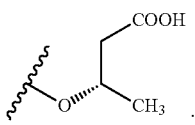
In an embodiment, $R^1$ is
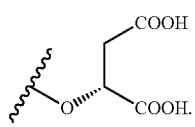
In an embodiment, $R^1$ is
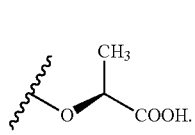 [SMILES: *O[C@@H](C)C(=O)O]
In an embodiment, $R^1$ is
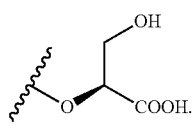 [SMILES: *O[C@@H](CO)C(=O)O]

In an embodiment, $R^1$ is

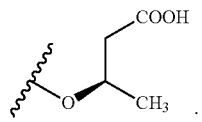 [SMILES: *O[C@H](C)CC(=O)O]

In an embodiment, $R^1$ is

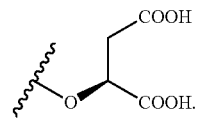

In an embodiment, when an asymmetric center is present in $R^1$, the compound is a mixture of the two enantiomers.
In an embodiment, when an asymmetric center is present in $R^1$, the compound is the S enantiomer.
In an embodiment, when an asymmetric center is present in $R^1$, the compound is the R enantiomer.
In an embodiment, $R^2$ is —OH.
In an embodiment, $R^2$ is $N_3$.
In an embodiment, $R^2$ is —N(H)C(=O)CH$_3$.
In an embodiment, $R^1$ and $R^2$ together with the carbon atoms to which they are attached form

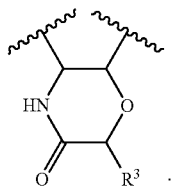

In an embodiment, $R^1$ and $R^2$ together with the carbon atoms to which they are attached form

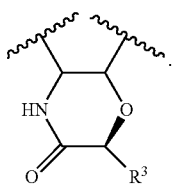

In an embodiment, $R^1$ and $R^2$ together with the carbon atoms to which they are attached form

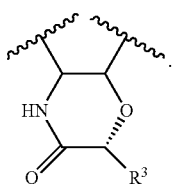

In an embodiment, $R^3$ is —H.
In an embodiment, $R^3$ is —CH$_3$.
In an embodiment, $R^3$ is —CH$_2$C(=)OH.
In an embodiment, $R^3$ is —CH$_2$OH.

In an embodiment, the compound is

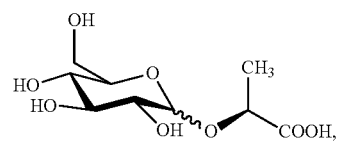

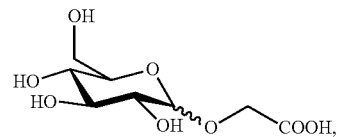

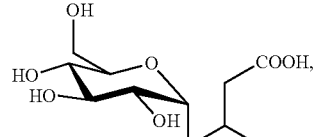

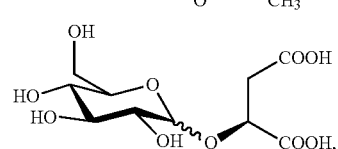

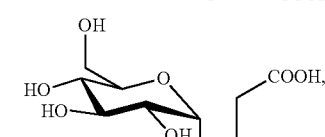

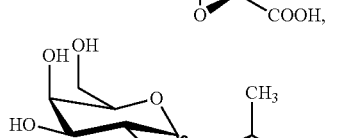

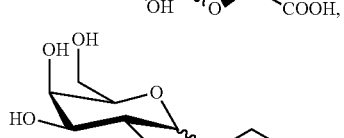

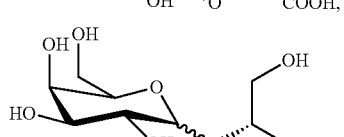

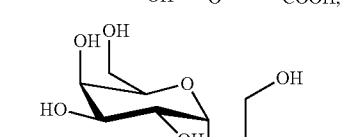

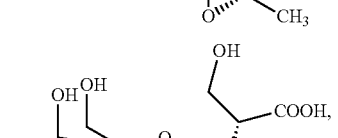

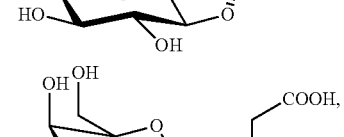

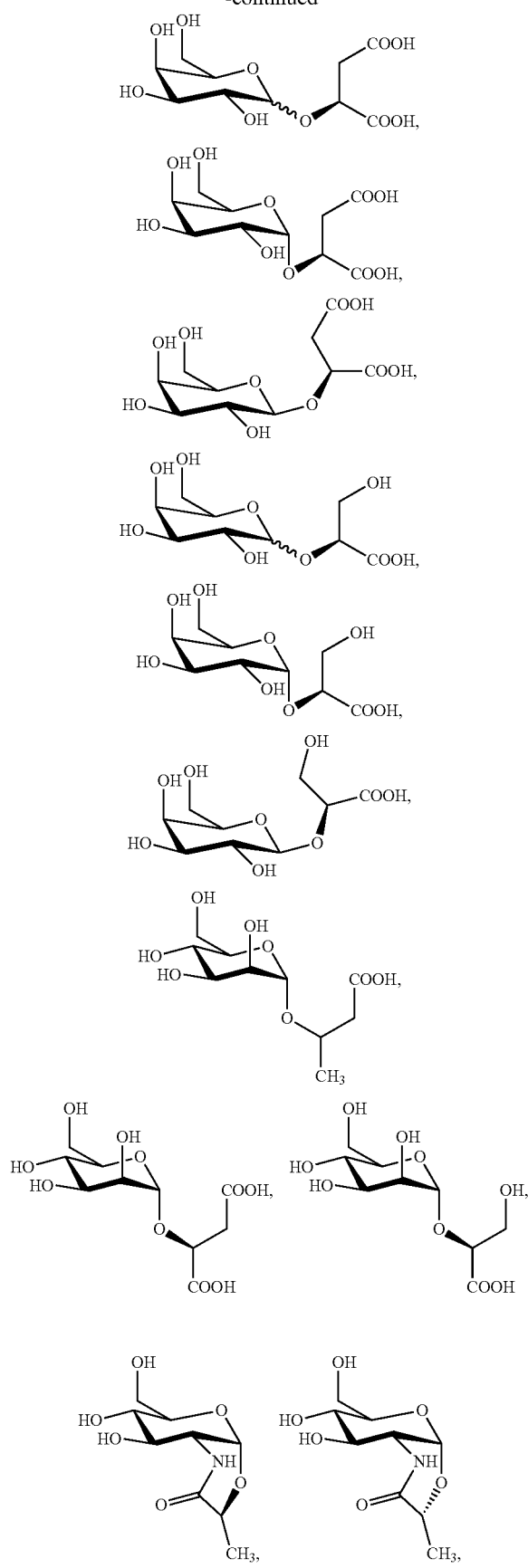

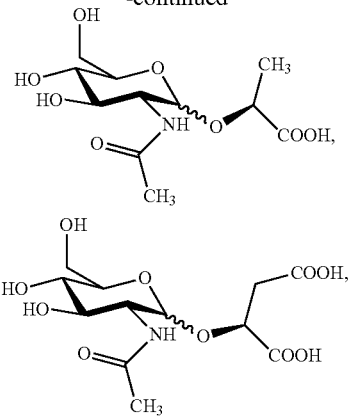

or a salt thereof.

In an embodiment, the compound is any one compound of the previous embodiment or a salt thereof.

In an embodiment, the compound is in the form of a salt.

In an embodiment, the compound is in the form of a pharmaceutically acceptable salt.

In an embodiment, the compound is in the form of a potassium salt.

In an embodiment, the compound is in the form of a sodium salt.

The invention also provides a composition comprising at least one compound of the invention, or a salt thereof, and a biological material.

In an embodiment, the composition is a liquid. In an embodiment, the composition is a solid. In an embodiment, the composition is lyophilized. In an embodiment, the composition is freeze-dried.

In an embodiment, the composition is a liquid and the at least one compound of the invention is present in the composition at a concentration of 0.01 to 1 M. In an embodiment, the at least one compound of the invention is present in a concentration of 0.1 to 0.5 M. In an embodiment, the at least one compound of the invention is present in a concentration of 0.01 to 1 M. In an embodiment, the at least one compound of the invention is present in the composition in a concentration of 0.1 M, 0.2 M, 0.25 M, 0.3 M, 0.4 M, or 0.5 M.

In an embodiment, the composition is a solid which was prepared by drying a liquid composition of the invention.

In an embodiment, the composition comprises at least one other compatible solute in addition to the at least one compound of the invention. The at least one other compatible solute can be, for example, at least one other compatible solute known in the art. In compositions having at least one other compatible solute and/or more than one compound of the invention, the amount of the other compatible solute and/or the amount of each compound of the invention necessary to stabilize the biological material may be less than the amount of each agent necessary to stabilize the biological material alone.

In an embodiment, the composition further comprises one or more salts in addition to the at least one compound of the invention. In an embodiment, the one or more additional salts are pharmaceutically acceptable salts. In an embodiment, the one or more salts comprises potassium acetate.

In an embodiment, the composition is a pharmaceutical composition, a cosmetic, or a food product.

In an embodiment, the biological material is a nucleic acid, a polypeptide, a whole cell, a virus, a virus like particle, a cell membrane, a cell component, a liposome, a tissue, or a mixture of any of the foregoing. In an embodiment, the biological material comprises one, two, three, or more species of biological material.

In an embodiment, biological material is one or more species of nucleic acids. In an embodiment, the nucleic acid is RNA, DNA, or a mixture of RNA and DNA. In an embodiment, the RNA is single stranded RNA. In an embodiment, the RNA is double stranded. In an embodiment, the RNA is mRNA. In an embodiment, the RNA is an antisense oligonucleotide. In an embodiment, the DNA is double stranded. In an embodiment, the DNA is single stranded.

In an embodiment, the biological material is one or more species of whole cells.

In an embodiment, the biological material is a polypeptide.

In an embodiment, the polypeptide is an enzyme, an antibody, a plasma protein, or a hormone.

In an embodiment, the polypeptide is insulin, malate dehydrogenase, staphylococcal nuclease or lysozyme. In an embodiment, the polypeptide is insulin.

In an embodiment, the polypeptide is a recombinant polypeptide. In an embodiment, the polypeptide is isolated from a yeast or mammalian cell culture.

In an embodiment, polypeptide is not a recombinant polypeptide. In an embodiment, the polypeptide is isolated from a plant, an animal, a fungus, or a bacteria. In an embodiment, the polypeptide is an animal or human serum polypeptide.

In an embodiment, the composition further comprises a buffer.

The invention also provides a method of stabilizing a biological material, comprising adding at least one compound of the invention, or a salt thereof, to a solution containing the biological material to form a stabilized solution.

In an embodiment, the method further comprises a step of drying the stabilized solution.

In an embodiment, the drying is spray-drying or lyophilization.

In an embodiment, the at least one compound of the invention or a salt thereof is selected based upon the properties of the biological material to be stabilized. For example, if the biological material is a protein, a compound of the invention, or a combination of compounds of the invention may be selected based upon the hydrophobicity and/or hydrophilicity of the surface of the protein.

The invention also provides a compound of the invention or a salt thereof for stabilizing a biological material.

The invention also provides a use of the compound of the invention or a salt thereof for stabilizing a biological material.

In an embodiment, stabilizing is protecting a biological material from denaturation. In an embodiment, stabilizing is increasing the melting temperature of a biological material. In an embodiment, stabilizing is protecting a biological material from dessication. In an embodiment, stabilizing is protecting a biological material from aggregation. In an embodiment, stabilizing is protecting a biological material from heat. In an embodiment, stabilizing is protecting a biological material from freezing. In an embodiment, stabilizing is protecting a biological material during drying. In an embodiment, stabilizing is increasing the shelf-life of a biological material.

The invention also provides a diagnostic kit comprising a compound of the invention or a salt thereof.

In an embodiment, the diagnostic kit is a microarray, a biosensor, or an enzymatic preparation. In an embodiment, the microarray, biosensor, or enzymatic preparation comprises an immobilized biological material. The compatible solutes of the invention can be used in methods known in the art which make us of compatible solutes to improve the performance of techniques using immobilized biological materials. See, for example, PCT International Application Publication No. WO/2007/097653.

The invention also provides a cosmetic or other dermatological composition comprising a compound of the invention, or a salt thereof, and an excipient suitable for topical administration to humans or animals.

In an embodiment, the cosmetic or dermatological composition comprises one or more biological materials.

The invention also provides compounds, compositions, methods, and uses as described above, wherein the compound is any compound listed in Table 6 or 7, or a salt thereof. For example, this invention provides a composition for stabilizing a biological material comprising one or more of the compounds listed in Tables 6 and 7 and the biological material. As another example, this invention provides a method of stabilizing a biological material, comprising adding at least one compound listed in Tables 6 and 7, or a salt thereof, to a solution containing the biological material to form a stabilized solution.

The specific embodiments and examples described herein are illustrative, and many variations can be introduced on these embodiments and examples without departing from the spirit of the disclosure or from the scope of the appended claims. Elements and/or features of different illustrative embodiments and/or examples may be combined with each other and/or substituted for each other within the scope of this disclosure and appended claims.

Each of the embodiments described herein as being applicable to or including a compound of the invention is equally applicable to a salt of the compound.

For the foregoing embodiments, each embodiment disclosed herein is contemplated as being applicable to each of the other disclosed embodiments.

By any range disclosed herein, it is meant that all tenth and integer unit amounts within the range are specifically disclosed as part of the invention. Thus, for example, 0.1 M to 0.5 M means that 0.1 M, 0.2 M, 0.3 M, 0.4 M, and 0.5 M are embodiments within the scope of the invention.

This invention will be better understood by reference to the Examples which follow, which are set forth to aid in an understanding of the subject matter but are not intended to, and should not be construed to, limit in any way the claims which follow thereafter.

Example 1: Synthesis of Novel Compatible Solutes

A chemical library based on sugar derivatives was prepared in order to identify new organic compounds with increased protein stabilization properties. The diversity of the analogue structures was introduced by using different hexoses, such as glucose, galactose, mannose and glucosamine, and by using different glycosyl acceptors during the glycosylation reaction.

Galactose and glucosamine analogues were synthesized in addition to mannosides and glucosides in order to assess the contribution of the sugar structure for the stabilization effect. To our knowledge, only one galactose containing compatible solute has been isolated from hyperthermophiles, the β-galactopyranosyl-5-hydroxylysine (GalHl) from *Thermococcus litoralis*:

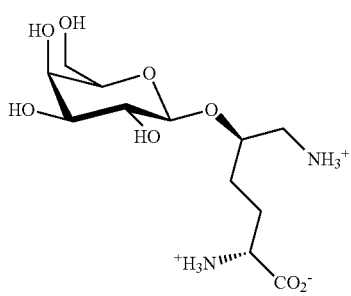

Several amino acids, like glutamate, proline, and glutamine, can function as compatible solutes in many mesophilic organisms and both α- and β-amino acids are used for osmoadaptation (Costa 1998). In order to determine if an amino group or the extra charge would enhance the stabilisation effect glucosamine derivatives were synthesized. To our knowledge, only one glucosamine containing compatible solute has been isolated from hyperthermophiles, di-N-acetyl-glucosamine phosphate (DAGAP) from *Rubrobacter xylanophilus*:

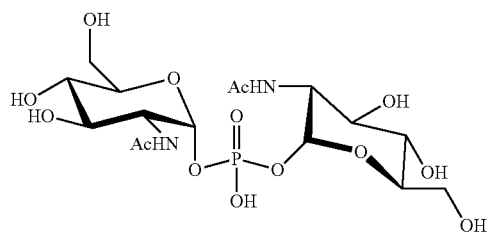

(Empadinhas 2007).

DAGAP is structurally similar to the phosphodiester compatible solutes found in hyperthermophiles, like DIP or DGP, however, the role as a compatible solute has been refuted due to the concentrations that are too low to contribute to the cell's osmotic balance.

All of the glycosyl acceptors chosen for this study are charged and structurally related to glycerate with point modifications, such as more or less carbon atoms, loss of a hydroxyl group, an additional carboxylic group and the configuration at the asymmetric center, when present:

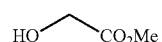

Methyl glycolate

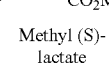

Methyl (S)-lactate

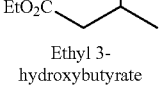

Ethyl 3-hydroxybutyrate

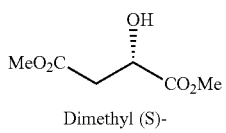

Dimethyl (S)-malate

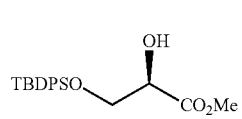

Methyl (2R)-3-O-tert-butyldiphenylsilyl-2,3-hidroxypropanoate

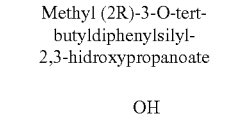

Methyl (2S)-3-O-tert-butyldiphenylsilyl-2,3-hidroxypropanoate

For the synthesis of the glucose and galactose derivatives, thioglycoside donors 1 and 19 were synthesized. The results obtained for the glycosylation reaction of donors 1 and 19 with the glycosyl acceptors above using NIS/TfOH system (Lourenco 2009) in dichloromethane are described in Table 1. All acceptors were commercially available with exception of the methyl glycerate derivatives 9 and 135, which were synthesised according to the experimental procedures reported for D-serine (Lourenco 2009; Lok 1976).

Scheme 1
Glycosylation reaction using thioglycoside donors 1 and 19

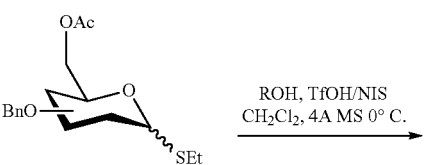

1: Glucose
19: Galactose

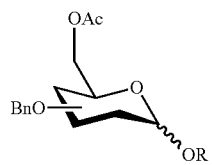

Reactions gave a mixture of anomers for most of the glycosyl acceptors. This provided the opportunity to test α and β anomers separately to determine the importance of the stereochemistry of the anomeric position for the stabilization effect. This was the case for the D/L-glycerate and malate galactosyl derivatives.

TABLE 1

Results obtained for the glycosylation reaction with the thioglycoside donors 1 and 19.

| ROH | Donor | Product | Yield | α/β |
|---|---|---|---|---|
| 4 | 1 | 10 | 91 | 4:1 |
| | 19 | 32 | 87 | 3:1 |
| 7 | 1 | 13 | 93 | 4:1 |
| | 19 | 34 | 95 | 3:1 |
| 9 | 19 | 35 | 88 | 2:1 |
| 133 | 1 | 136 | 84 | 9:1[a] |
| | 19 | 137 | 95 | 3:1[a] |
| 134 | 1 | 138 | 94 | 7:1 |
| | 19 | 139 | 87 | 5:1 |
| 135 | 1 | 140 | 98 | >10:1 |
| | 19 | 141 | 88 | 2.6:1 |

[a]Calculated after deprotection of the acetate group.

After the successive removal of the protective groups using common organic reactions, such as methanolysis of the acetates, fluorolysis of the silyl ether in the case of the glycerate analogues (compounds 35, 140 and 141) and hydrolysis of the ester group (Scheme 2), the desired products were obtained (Table 2).

Scheme 2
General deprotection scheme for the glucose and galactose analogues.

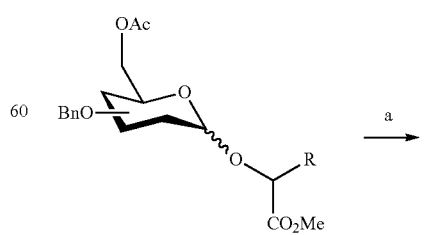

R: H, CH$_3$, CH$_2$OTBDPS, CH$_2$CO$_2$Me.

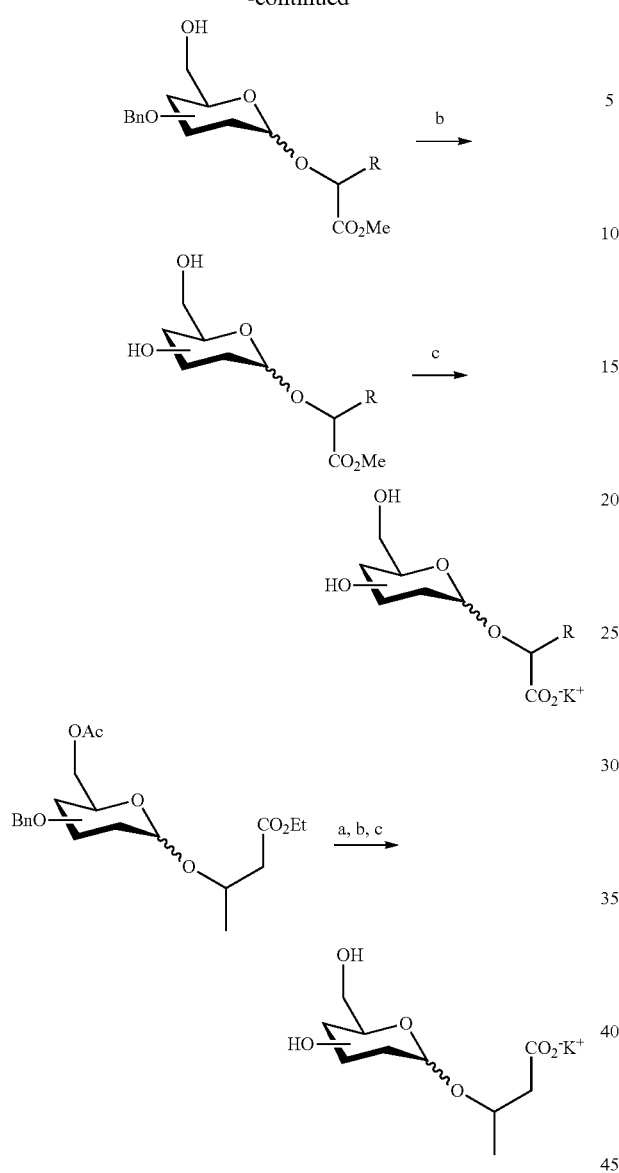
TABLE 2
Final products and overall yields[a] for glucose and galactose derivatives.
| Compound number | Final Product | Yield (%)[a] |
|---|---|---|
| 10 | 142 | 78 |
| 32 | 143 | 83 |
| 13 | 144 | 73 |
| 34 | 145 | 77 |
| 35 | 146 α / 147 β | 61 / 21 |
| 136 | 148 | 68 |
| 137 | 149 | 86 |
| 138 | 150 | 42 |
a) NaOMe, MeOH, 0° C.-r.t. b) H₂(g), Pd/C, 50 psi, AcOEt, r.t. c) KOH/H₂O, r.t.

TABLE 2-continued

Final products and overall yields[a] for glucose and galactose derivatives.

| Compound number | Final Product | Yield (%)[a] |
|---|---|---|
| 139 | 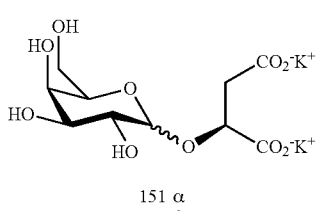<br>151 α<br>152 β | 57<br>16 |
| 140 | 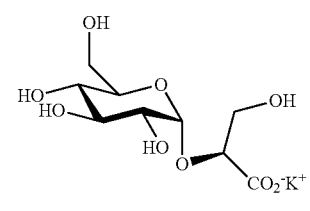<br>153 | 60 |
| 141 | 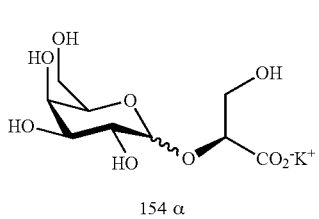<br>154 α<br>155 β | 43<br>14 |

[a]Calculated from the glycosylation reaction.

Overall the products were successfully obtained in good yields and the α anomer was the major product. Although in some cases a mixture of α and β anomers was obtained (enriched in α), they were used for a preliminary screening where the most promising compounds would then be tested separately. The lowest yields were obtained for the derivatives of the dimethyl (S)-malate (150, 151 and 152, Table 2) due to the use of base in the removal of the acetates and in the hydrolysis of the methyl ester, which promoted the hydrolysis of the anomeric position, by elimination of the malate moiety. This problem has been reported in the literature in the synthesis of bacillithiol (BSH) (Sharma 2011). To minimize the elimination of the malate moiety, careful ester hydrolysis left traces of the mono-ester in the final product.

For the synthesis of the 1,2-trans mannosides, the C-2 acyl neighboring group participation strategy was applied using acetates as protecting groups, and trichloroacetimidates as glycosyl donors, which are relatively fast to prepare and inexpensive. Glycosylation reaction between the mannose trichloroacetimidate donor 103 and the glycosyl acceptors, using $BF_3OEt_2$ as the promoter, afforded as expected exclusively the α-products. The results obtained for the glycosylation reaction with the mannose donor 103 are presented in Table 3.

Scheme 3
Glycosylation reaction with the mannose trichloroacetimide donor 103.

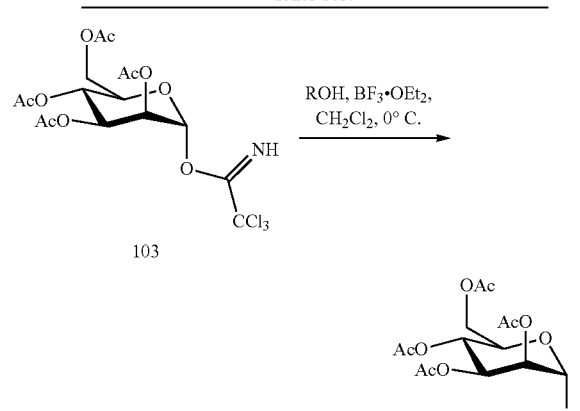

TABLE 3

Results obtained for the glycosylation reaction with the mannose trichloroacetimide donor 103.

| ROH | Product | Yield (%) |
|---|---|---|
| 133 | 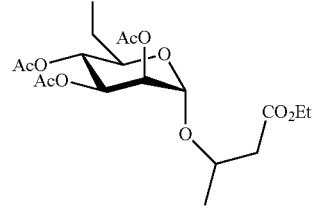<br>156 | 91 |
| 134 | 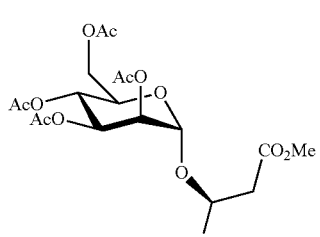<br>157 | 88 |
| 135 | 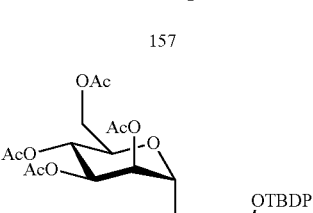<br>158 | 73 |

Successive removal of the protective groups using common organic reactions (Scheme 4), afforded the desired products (Table 4) in good overall yields.

Scheme 4
General deprotection scheme for the mannose analogues.

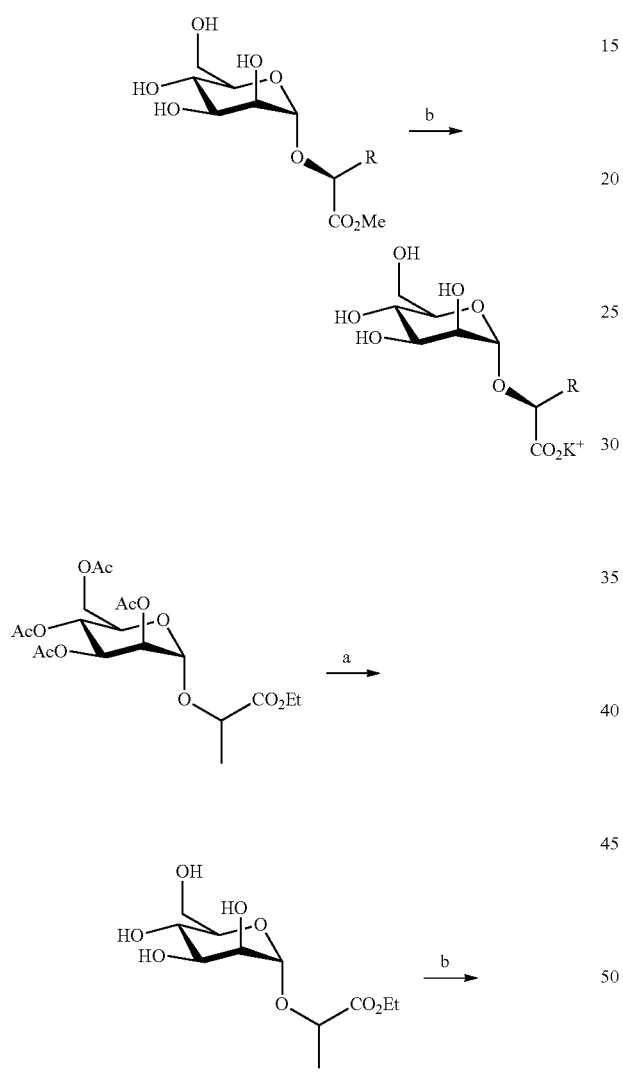

R: CH$_2$OTBDPS, CH$_2$CO$_2$Me.

a) NaOMe, MeOH, 0° C.-r.t. b) KOH/H$_2$O, r.t.

TABLE 4

Final products and overall yields[a] for mannose products.

| Compound Number | Final Product | Overall Yield (%)[a] |
|---|---|---|
| 156 | 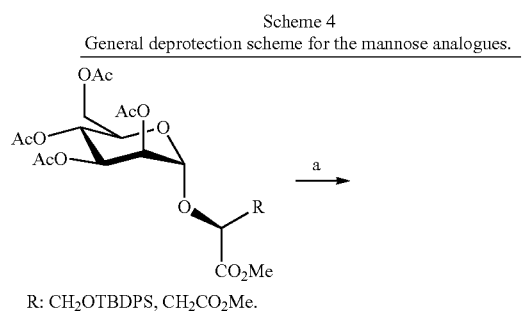 | 73 |
| 157 | | 69 |
| 158 | | 50 |

159, 160, 161

[a]Calculated from the glycosylation reaction

Hydrolysis of the acetate groups and of the methyl ester of mannosyl dimethyl (S)-malate derivative presented the same problem described above for the glucose and galactose derivatives.

The 1,2-cis glucosamine derivatives were synthesised from the 2-azido-2-deoxythioglucoside donor 90, and the glycosylation reaction with the glycosyl acceptors conducted in a mixture of CH$_2$Cl$_2$/Et$_2$O (4:1) at −10° C. and using NIS/TfOH as promotor. The results are presented in Table 5.

Scheme 5
Glycosylation reaction with the 2-azido-2-deoxythioglucoside donor 90.

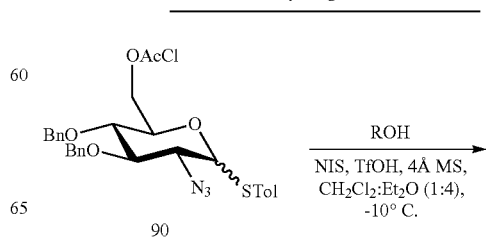

90

ROH
NIS, TfOH, 4Å MS,
CH$_2$Cl$_2$:Et$_2$O (1:4),
−10° C.

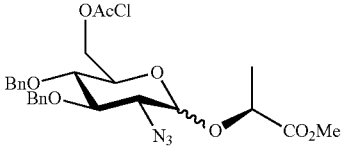

TABLE 5

Results obtained for the glycosylation reaction with the 2-azido-2-deoxythioglucoside donor 90.

| ROH | Product | Yield (%) | α/β |
|---|---|---|---|
| 4 | 95 | 86 | 8.7:1 |
| 7 | 96 | 76 | 12:1 |
| 9 | 97 | 84 | >10:1 |
| 134 | 162 | 86 | 1:0 |

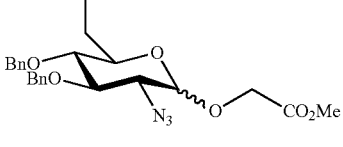

The α anomer was the major product for all of the acceptors used. After methanolysis of the acetate group and in the case of the glycerate derivative fluorolysis of the silyl ether, catalytic hydrogenation of the benzyl group with simultaneous reduction of the azide promoted the formation of an undesired cyclic amide (Scheme 6). This effect was only observed for the α anomers.

Scheme 6
Hydrogenation of the 2-azido-2-deoxyglucoside derivatives.

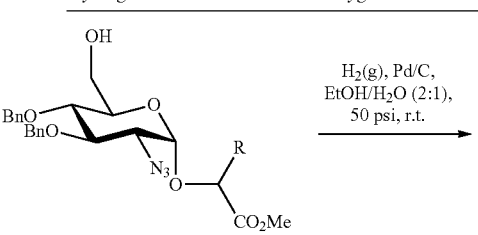

163: R = Me
164: R = H
165: R = CH$_2$OH
166: R = CH$_2$CO$_2$Me

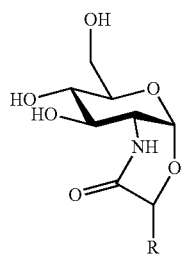

167: R = Me, 84%
168: R = H, 81%
169: R = CH$_2$OH, 80%
170: R = CH$_2$CO$_2$H, 87%

Since charge is important for the stabilisation effect, to overcome this problem previous reduction of the azide using a Staudinger reaction, followed by protection of the resulting amine group with acetate (Scheme 7) blocked the amine and avoided cyclisation. After removal of the protecting groups and hydrolysis of the methyl ester the final N-acetyl glucosamine derivatives were obtained.

Scheme 7
Synthesis of the N-acetyl glucosamine derivatives.

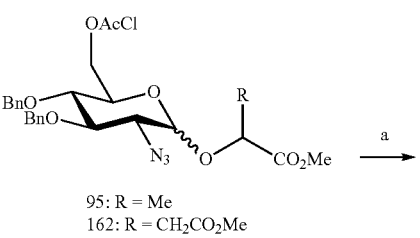

95: R = Me
162: R = CH$_2$CO$_2$Me

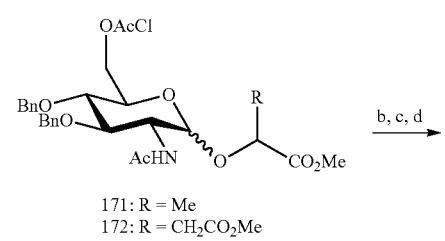

171: R = Me
172: R = CH$_2$CO$_2$Me

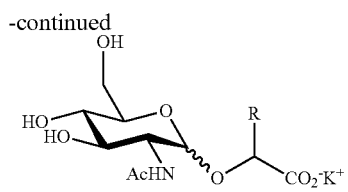

173: R = Me, 46% (after 4 steps)
174: R = CH$_2$CO$_2^-$K$^+$, 33% (after 4 steps)

a) (i) Ph$_3$P, THF, AcOH, 0° C.-r.t. (ii) Ac$_2$O, 0° C. b) NaOMe, MeOH, 0° C. c) H$_2$ (g), PdC, AcOEt, 50 psi, r.t. d) KOH/H$_2$O, r.t.

Experimental Details

Experiment 1. Synthesis of Ethyl 6-O-acetyl-2,3,4-tri-O-benzyl-1-thio-α/β-D-glucopyranoside (1)

The synthesis of compound 1 was carried out according to the procedure described in the literature (Lourenco 2009).

Experiment 2. General Glycosylation Procedure

A suspension of thioglycoside donor (0.15 mmol), acceptor (0.15 mmol) and 4 Å MS in the solvent/mixture of solvents indicated (1 mL) was stirred for 1 h at room temperature then cooled to 0° C. N-Iodosuccinimide (0.19 mmol) and TfOH (0.9 μL) were added at 0° C. and when the reaction was complete (TLC), 10% Na$_2$S$_2$O$_3$ aqueous solution (2 mL) and saturated aqueous NaHCO$_3$ (1 mL) were added and the mixture was extracted with CH$_2$Cl$_2$ (3×5 mL); the combined organic phases were dried (MgSO$_4$), filtered and the solvent was removed under vacuum. The crude product was purified by preparative TLC (3:7, EtOAc/Hex). The α/β ratio of the isolated product was measured by $^1$H NMR (400 MHz, CDCl$_3$) spectra.

Experiment 3. Synthesis of Methyl (2S)-2-(6-O-acetyl-2,3,4-tri-O-benzyl-α/β-D-glucopyranosyl)propanoate (10)

The glycosylation reaction of donor 1 with acceptor 4 was performed according to the procedure described in experiment 2.

Experiment 4. Synthesis of Methyl 2-(6-O-acetyl-2,3,4-tri-O-benzyl-α/β-D-glucopyranosyl)acetate (13)

The glycosylation reaction of donor 1 with acceptor 7 was performed according to the procedure described in experiment 2.

Experiment 5. Synthesis of Ethyl 6-O-acetyl-2,3,4-tri-O-benzyl-1-thio-α/β-D-galactopyranoside (19)

To a stirred solution of methyl α-D-galactopyranoside (2.0 g, 10.3 mmol) in DMF (20 mL) was added benzyl bromide (6.3 mL, 51.5 mmol). The mixture was cooled to 0° C. and sodium hydride (1.48 g, 61.8 mmol) was added portion-wise. The reaction was kept over-night at room temperature (r.t.) and after complete conversion of the starting material MeOH was added at 0° C. The mixture was extracted with Et$_2$O and the combined organic phases dried, filtered and concentrate. Purification by flash column chromatography on silica gel (10:90, EtOAc/Hex) afforded the product as a viscous colourless foam (5.14 g, 90%).

Concentrated sulphuric acid (1.0 mL) was added drop-wise to a stirred solution of the methyl tetra-O-benzylgalactopyranoside (5.72 g, 10.7 mmol) in acetic acid/acetic anhydride (1:1, 50 mL) at 0° C. After complete conversion of the starting material the reaction mixture was quenched with saturated NaHCO$_3$ solution and ice-cold distilled water until pH 7. The mixture was extracted with EtOAc (3×70 mL) and the combined organic dried, filtered and concentrated in vacuum. The residue was purified by flash column chromatography on silica gel (20:80, EtOAc/Hex) to give the diacetate (4.29 g, 75%, α:β=3.7:1) as a viscous colourless foam.

Ethanethiol (1.56 mL, 20.7 mmol) was added to a stirred solution of diacetate (3.69 g, 6.9 mmol) in DCM (30 ml). The reaction mixture was cooled to 0° C. and boron trifluoride diethyl etherate (1.31 mL, 10.35 mmol) added drop-wise. After complete conversion of starting material the reaction mixture was diluted with CH$_2$Cl$_2$ (2×40 mL) and quenched with saturated NaHCO$_3$ solution until pH 7.

The aqueous phase was extracted with CH$_2$Cl$_2$ (2×40 mL) and the combined organic extracts dried, filtered and concentrated in vacuum. The residue was purified by flash column chromatography (20:80, EtOAc/Hex) to give the thiogalactoside 19 (3.39 g, 91%, α/β=2.4:1) as a viscous colourless foam.

Experiment 6. Synthesis of Methyl (2S)-2-(6-O-acetyl-2,3,4-tri-O-benzyl-α/β-D-galactopyranosyl)propanoate (32)

The glycosylation reaction of donor 19 with acceptor 4 was performed according to the procedure described in experiment 2.

Experiment 7. Synthesis of Methyl 2-(6-O-acetyl-2,3,4-tri-O-benzyl-α/β-D-galactopyranosyl)acetate (34)

The glycosylation reaction of donor 19 with acceptor 7 was performed according to the procedure described in experiment 2.

Experiment 8. Synthesis of Methyl 3-O-tert-butyldimethylsilyl-(2R)-2-O-(6-O-acetyl-2,3,4-tri-O-benzyl-α/β-D-galactopyranosyl)-2,3-dihydroxypropanoate (35)

The glycosylation reaction of donor 19 with acceptor 9 was performed according to the procedure described in experiment 2.

Experiment 9. Synthesis of Phenyl 3,4,6-tri-O-acetyl-2-azido-2-deoxy-1-thio-α/β-D-glucopyranoside (85)

To a solution of 1,3,4,6-tetra-O-acetyl-2-azido-2-deoxy-α/β-D-glucopyranose (Goddard-Borger 2007) (6.42 g, 17.2 mmol) and thiophenol (3.55 mL, 34.4 mmol) in CH$_2$Cl$_2$ (60 mL) at 0° C. was added and BF$_3$OEt$_2$ (9.81 mL, 77.4 mmol). The reaction mixture was stirred at r.t. for 48 hours, then diluted with CH$_2$Cl$_2$ and washed with NaHCO$_3$. The aqueous phase was extracted with CH$_2$Cl$_2$ and the combined organic phases were dried with MgSO$_4$, filtered and concentrated under vacuum. The crude was purified by flash column chromatography on silica gel (30:70, EtoAc/hexane)

to afford 85 (5.40 g, 74%, α/β=2.5:1) as a colourless viscous foam, and to recover the initial tetraacetate (1.30 g, 20%).

Experiment 10. Synthesis of p-Tolyl 3,4,6-tri-O-acetyl-2-azido-2-deoxy-1-thio-α/β-D-glucopyranoside (86)

To a solution of 1,3,4,6-tetra-O-acetyl-2-azido-2-deoxy-α/β-D-glucopyranose (Goddard-Borger 2007) (3.87 g, 10.4 mmol) and p-toluenethiol (2.57 g, 20.7 mmol) in $CH_2Cl_2$ (60 mL) at 0° C. was added and $BF_3OEt_2$ (6.57 mL, 51.8 mmol). The reaction mixture was stirred at r.t. for 60 hours, then diluted with $CH_2Cl_2$ and washed with $NaHCO_3$. The aqueous phase was extracted with $CH_2Cl_2$ and the combined organic phases were dried with $MgSO_4$, filtered and concentrated under vacuum. The crude was purified by flash column chromatography on silica gel (30:70, EtOAc/hexane) to afford 85 (2.26 g, 50%, α/β=1.8:1) as a colourless viscous foam, and to recover the initial tetraacetate (1.69 g, 44%).

Experiment 11. Synthesis of Phenyl 2-azido-6-O-tert-butyldiphenylsilyl-2-deoxy-1-thio-α/β-D-glucopyranoside (87)

A solution of NaOMe 1N (6.73 mL, 6.73 mmol) in MeOH was added to a stirred solution of 85 (4.75 g, 11.21 mmol) in MeOH (20 mL) at 0° C. After 3 hours the starting material had been consumed. The reaction mixture was diluted with MeOH and Dowex-$H^+$ resin was added until neutral pH. Filtration and evaporation of the solvents afforded the triol (3.23 g, 97%) as a viscous gum. To a solution of triol (2.46 g, 8.27 mmol) in pyridine (20 mL) at r.t. was added TBDPSCl (2.36 mL, 9.10 mmol), followed by a catalytic amount of DMAP. The mixture was stirred overnight, then quenched with $H_2O$ (20 mL), extracted with $CH_2Cl_2$ (3×20 mL) and the combined organic phases were dried ($MgSO_4$) and concentrated. Purification by flash column chromatography (30:70 AcOEt/hexane) afforded the product 87 (4.12 g, 93%, α/β=1.8:1) as a white solid.

Experiment 12. Synthesis of p-Tolyl 2-azido-6-O-tert-butyldiphenylsilyl-2-deoxy-1-thio-α/β-D-glucopyranoside (88)

The procedure of experiment 11 was applied to compound 86 affording compound 88 as a colourless viscous gum in 98% yield (α/β=1.8:1) over the two steps.

Experiment 13. Synthesis of Phenyl 6-O-acetyl-2-azido-3,4-di-O-benzyl-2-deoxy-1-thio-α/β-D-glucopyranoside (89)

To a stirred solution of 87 (3.91 g, 7.30 mmol) and benzyl bromide (1.97 mL, 22.6 mmol) in DMF (15 mL) at 0° C. was added portion-wise sodium hydride (0.45 g, 18.6 mmol). After 2 hours, MeOH was added at 0° C. and the reaction mixture was quenched with a saturated aqueous solution and extracted with $Et_2O$. The combined organic phases were dried with $MgSO_4$, filtered and evaporated in vacuum. Purification by flash column chromatography (10:90 AcOEt/hexane) afforded the dibenzylated product (4.45 g, 85%) as a white solid, and the tribenzylated product 92 (0.31 g, 7%) as a viscous gum.

To a solution of the dibenzylated product (2.42 g, 3.38 mmol) in THF (10 mL) at r.t. was added TBAF (1.15 g, 4.39 mmol). The reaction mixture was stirred for 3 hours and then water was added. The mixture was extracted with AcOEt (3×20 mL), dried ($MgSO_4$) and concentrated to furnish a yellow viscous residue. Purification by flash column chromatography (30:70, AcOEt/hexane) afforded the alcohol (1.43 g, 88%) as a viscous gum.

To a stirred solution of the alcohol (1.396 g, 2.92 mmol) in pyridine (5 mL) at 0° C. was added acetic anhydride (0.55 mL, 5.85 mmol) and a catalytic amount of DMAP. After complete conversion of the starting material water was added. The mixture was extracted with EtOAc, dried ($MgSO_4$) and concentrated to furnish a viscous residue. Filtration through celite with a mixture of EtOAc/hexane (10/90) afforded the product 89 as a viscous colourless gum (1.38 g, 91%, α:β=1.4:1).

Experiment 14. Synthesis of Phenyl 2-azido-3,4,di-O-benzyl-6-O-chloroacetyl-2-deoxy-1-thio-α/β-D-glucopyranoside (90)

The procedure of experiment 13 was applied to compound 87 using chloroacetic anhydride and affording compound 90 as a colourless viscous gum in 66% (α/β=1.6:1) yield over the three steps. Characterisation data of compound 90 identical to the literature (Csiki 2010).

Experiment 15. Synthesis of p-Tolyl 2-azido-3,4,di-O-benzyl-6-O-chloroacetyl-2-deoxy-1-thio-α/β-D-glucopyranoside (91)

The procedure of experiment 13 was applied to compound 88 using chloroacetic anhydride and affording compound 91 as a colourless viscous gum in 82% yield (α/β=1:1) over the three steps.

Experiment 16. Synthesis of Methyl (2S)-2-(2-azido-3,4,di-O-benzyl-6-O-chloroacetyl-2-deoxy-α/β-D-glucopyranosyl)propanoate (95)

The glycosylation reactions of donor 90 and 91 with acceptor 4 were performed according to the procedure described in experiment 2.

Experiment 17. Synthesis of Methyl 2-(2-azido-3,4,di-O-benzyl-6-O-chloroacetyl-2-deoxy-α/β-D-glucopyranosyl)acetate (96)

The glycosylation reaction of donor 91 with acceptor 7 was performed according to the procedure described in experiment 2.

Experiment 18. Synthesis of Methyl (2R)-tert-butyldimethylsilyl-3-(2-azido-3,4,di-O-benzyl-6-O-chloroacetyl-2-deoxy-α/β-D-glucopyranosyl)-2,3-dihydroxyropanoate (97)

The glycosylation reaction of donor 91 with acceptor 9 was performed according to the procedure described in experiment 2.

Experiment 19. Synthesis of 2,3,4,6-Tetra-O-acetyl-α-D-mannopyranosyl trichloroacetimidate (103)

The synthesis of compound 103 was carried out according to the procedure described in the literature (Hanessian 1997).

Experiment 20. Synthesis of Ethyl 3-O-(6-O-acetyl-2,3,4-tri-O-benzyl-α/β-D-glucopyranosyl)-3-hydroxybutyrate (136)

A suspension of thioglucoside donor 1 (0.815 g, 1.52 mmol), ethyl 3-hydroxybutyrate 133 (0.197 mL, 1.52 mmol) and 4 Å MS in $CH_2Cl_2$ (6 mL) was stirred for 1 h at room temperature then cooled to 0° C. N-Iodosuccinimide (0.434 g, 1.93 mmol) and TfOH (0.112 mL) were added at 0° C. and when the reaction was complete, 10% $Na_2S_2O_3$ aqueous solution (6 mL) and saturated aqueous $NaHCO_3$ solution (3 mL) were added. The mixture was extracted with $CH_2Cl_2$ (3×6 mL), the combined organic phases were dried ($MgSO_4$), filtered and the solvent was removed under vacuum. The crude product was purified by flash column chromatography on silica gel (20:80, EtOAc/Hex) to afforded product 136 as a viscous colourless foam (0.771 g, 84%).

Experiment 21. Synthesis of Ethyl 3-O-(6-O-acetyl-2,3,4-tri-O-benzyl-α/β-D-galactopyranosyl)-3-hydroxybutyrate (137)

The glycosylation reaction of thiogalactoside donor 19 (0.638 g, 1.19 mmol) and ethyl 3-hydroxybutyrate 133 (0.170 mL, 1.31 mmol) was performed according to the procedure described in experiment 20. The crude was purified by flash column chromatography on silica gel (20:80, EtOAc/Hex) affording the product 137 as a viscous colourless gum (0.685 g, 95%).

Experiment 22. Synthesis of Dimethyl (2S)-2-O-(6-O-acetyl-2,3,4-tri-O-benzyl-α/β-D-glucopyranosyl)-2-hydroxysuccinate (138)

The glycosylation reaction of thiogalactoside donor 1 (0.850 g, 1.58 mmol) and dimethyl (S)-malate 134 (0.208 mL, 1.58 mmol) was performed according to the procedure described in experiment 20. The crude was purified by flash column chromatography on silica gel (30:70, EtOAc/Hex) affording the product 138 as a viscous colourless gum (0.949 g, 94%, α/β=7:1).

Experiment 23. Synthesis of Dimethyl (2S)-2-O-(6-O-acetyl-2,3,4-tri-O-benzyl-α/β-D-galactopyranosyl)-2-hydroxysuccinate (139)

The glycosylation reaction of thiogalactoside donor 19 (1.20 g, 2.23 mmol) and dimethyl (S)-malate 134 (0.294 mL, 2.23 mmol) was performed according to the procedure described in experiment 20. The crude was purified by flash column chromatography on silica gel (30:70, EtOAc/Hex) affording the product 139 as a viscous colourless gum (1.235 g, 87%, α/β=5:1).

Experiment 24. Synthesis of Methyl 3-O-tert-butyldimethylsilyl-(2S)-2-O-(6-O-acetyl-2,3,4-tri-O-benzyl-α/β-D-glucopyranosyl)-2,3-dihydroxypropanoate (140)

The glycosylation reaction of thiogalactoside donor 1 (0.300 g, 0.56 mmol) and acceptor 135 (0.200 g, 0.56 mmol) was performed according to the procedure described in experiment 20. The crude was purified by flash column chromatography on silica gel (10:90, EtOAc/Hex) affording the product 140 as a viscous colourless gum (0.463 g, 98%, α/β>10:1).

Experiment 25. Synthesis of Methyl 3-O-tert-butyldimethylsilyl-(2S)-2-O-(6-O-acetyl-2,3,4-tri-O-benzyl-α/β-D-galactopyranosyl)-2,3-dihydroxypropanoate (141)

The glycosylation reaction of thiogalactoside donor 1 (0.300 g, 0.56 mmol) and acceptor 135 (0.200 g, 0.56 mmol) was performed according to the procedure described in experiment 20. The crude was purified by flash column chromatography on silica gel (10:90, EtOAc/Hex) affording the product 140 as a viscous colourless gum (0.463 g, 98%, α/β>10:1).

Experiment 26. Synthesis of Potassium (2S)-2-(α-D-glucopyranosyl)propanoate (142)

A solution of NaOMe 1N (0.443 mL, 0.443 mmol) in MeOH was added to a stirred solution of 10 (0.427 g, 0.74 mmol) in MeOH (4 mL) at 0° C. After 1 h the reaction mixture was neutralized with saturated aqueous $NH_4Cl$. The aqueous phase was extracted with EtOAc and the combined organic extracts were dried ($MgSO_4$), filtered and the solvent was removed. The crude product was purified by flash column chromatography on silica gel (30:70, EtOAc/Hex) to afford the α (0.310 g, 78%) and β-alcohol (0.027 g, 7%) as viscous colourless gums.

A solution of the α-alcohol (0.300 g, 0.56 mmol) in EtOAc was hydrogenated at 50 psi in the presence of Pd/C 10% (0.25 equiv). After 5 hours, the reaction mixture was filtered and the solvent was evaporated to afford the ester as a very viscous colourless foam (0.149 g, quantitative). A solution of 2 M KOH (0.28 mL) was added to a stirred solution of the ester (0.149 g, 0.56 mmol) in $H_2O$ (2 mL). After all of the starting material had been consumed, the pH was adjusted to 7 with 10% HCl and the solvent was evaporated to afford 142 as a viscous colorless foam (0.162 g, quantitative). $[α]^{20}_D$=+107.2 (c=0.60, $H_2O$). $^1H$ NMR ($D_2O$): δ 4.93 (d, J=3.9 Hz, 1H, H-1), 3.96 (q, J=6.8 Hz, 1H, C$\underline{H}$CH$_3$), 3.75-3.68 (m, 5H), 3.44 (dd, J=9.9 Hz, J=4.0 Hz, 1H, H-2), 3.35 (t, J=9.3 Hz, 1H, H-4), 1.28 (d, J=6.8 Hz, 3H, CHC$\underline{H}_3$) ppm. $^{13}C$ NMR (CDCl$_3$): δ 181.0 (CHCO$_2^-$), 97.3 (C-1), 75.5 (CHCH$_3$), 73.1 (C-3), 71.9 (C-5), 71.5 (C-2), 69.4 (C-4), 60.1 (C-6), 17.5 (CHCH$_3$) ppm.

Experiment 27. Synthesis of Potassium (2S)-2-(α/β-D-galactopyranosyl) propanoate (143)

The methanolysis of the acetate group of the galactoside 32 (1.720 g, 2.63 mmol) was performed according to the procedure described in experiment 26. The crude was purified by flash column chromatography on silica gel (40:60, EtOAc/Hex) affording the alcohol as a viscous colourless gum (1.350 g, 96%, α/β=3:1). After catalytic hydrogenation of the benzyl ethers (1.323 g, 2.46 mmol) and hydrolysis of the methyl ester according to the procedure described in experiment 23, the compound 143 was obtained as a viscous colorless foam (0.715 g, quantitative, α/β=3:1). FTIR (film) $v_{max}$: 1635 (C=O), 3332 (O—H) cm$^{-1}$. $^1H$ NMR (D$_2$O): δ 4.97 (d, J=3.9 Hz, H-1 (α)), 4.58 (q, J=7.0 Hz, C$\underline{H}$CH$_3$ (β)), 4.37 (d, J=7.7 Hz, H-1 (β)), 4.25 (q, J=6.9 Hz, C$\underline{H}$CH$_3$ (α)), 3.93-3.88 (m), 3.84-3.79 (m), 3.76-3.64 (m), 3.63-3.52 (m), 3.47 (dd, J=9.9, 7.7 Hz), 1.38 (d, J=7.0 Hz, CHC$\underline{H}_3$ (β)), 1.35 (d, J=6.8 Hz, CHC$\underline{H}_3$ (α)) ppm. $^{13}C$ NMR (CDCl$_3$): δ 187.3 (CHCO$_2^-$), 101.8 (C-1 (β)), 98.9 (C-1 (α)), 75.2, 73.7, 73.1, 72.6, 71.4, 70.7, 69.21, 69.07, 68.5, 68.0, 60.84, 60.80, 52.68, 52.62, 17.1 (CHCH$_3$) ppm.

Experiment 28. Synthesis of Potassium 2-(α/β-D-glucopyranosyl)acetate (144)

The methanolysis of the acetate group of the glucoside 13 (0.940 g, 1.66 mmol) was performed according to the procedure described in experiment 26. The crude was purified by flash column chromatography on silica gel (40:60, EtOAc/Hex) affording the alcohol as a viscous colourless gum (0.765 g, 88%, α/β=11:1). After catalytic hydrogenation of the benzyl ethers (0.715 g, 1.37 mmol) and hydrolysis of the methyl ester according to the procedure described in experiment 26, the compound 144 was obtained as a viscous colorless foam (0.378 g, quantitative, α/β=10:1). $^1$H NMR (D$_2$O): δ 4.88 (d, J=3.8 Hz, H-1 (α)), 4.41 (d, J=7.9 Hz, H-1 (β)), 4.22 (d, J=15.6 Hz, CHH'CO$_2^-$ (β)), 4.06 (d, J=15.5 Hz, CHH'CO$_2^-$ (α)), 4.03 (d, J=15.8 Hz, CH H'CO$_2^-$ (α)), 3.88 (d, J=15.5 Hz, CHH'CO$_2^-$ (β)), 3.79-3.61 (m), 3.46 (dd, J=9.8, 3.8 Hz), 3.34 (t, J=9.5 Hz) ppm. $^{13}$C NMR (CDCl$_3$): δ 177.4, 102.3 (C-1 (β)), 98.3 (C-1 (α)), 75.9 (β), 75.5 (β), 73.1, 71.9, 71.5, 69.5, 68.5 (CH$_2$CO$_2^-$ (β)), 66.8 (CH$_2$CO$_2^-$ (α)), 60.61 (C-6 (β)), 60.43 (C-6 (α)) ppm.

Experiment 29. Synthesis of Potassium 2-(α/β-D-galactopyranosyl)acetate (145)

The methanolysis of the acetate group of the galactoside 34 (1.079 g, 1.91 mmol) was performed according to the procedure described in experiment 26. The crude was purified by flash column chromatography on silica gel (40:60, EtOAc/Hex) affording the alcohol as a viscous colourless gum (0.800 g, 81%, α/β=2:1). After catalytic hydrogenation of the benzyl ethers (0.787 g, 1.50 mmol) and hydrolysis of the methyl ester according to the procedure described in experiment 26, the compound 145 was obtained as a viscous colorless foam (0.416 g, quantitative, α/β=2:1). $^1$H NMR (D$_2$O): δ 4.91 (d, J=3.9 Hz, H-1 (α)), 4.34 (d, J=7.7 Hz, H-1 (β)), 4.24 (d, J=15.6 Hz, CHH'CO$_2^-$ (β)), 4.06 (d, J=15.6 Hz, CHH'CO$_2^-$ (α)), 4.03 (d, J=15.6 Hz, CHH'CO$_2^-$ (β)), 3.92-3.84 (m), (d, J=15.6 Hz, CHH'CO$_2^-$ (α)), 3.75-3.71 (m), 3.69-3.58 (m), 3.52 (dd, J=10.0 Hz, J=7.6 Hz, H-2 (β)) ppm. $^{13}$C NMR (CDCl$_3$): δ 177.5, 102.9 (C-1 (β)), 98.3 (C-1 (α)), 75.2 (β), 72.6 (β), 71.1 (α), 70.8 (β), 69.5 (α), 69.2 (α), 68.6 (β), 68.5 (CH$_2$CO$_2^-$ (β)), 68.4 (α), 66.8 (CH$_2$CO$_2^-$ (α)), 61.15 (C-6 (α)), 60.95 (C-6 (β)) ppm.

Experiment 30. Synthesis of Potassium (2R)-2-O-(α/β-D-galactopyranosyl)-2,3-dihydroxypropanoate (146, 147)

The methanolysis of the acetate group of the galactoside 35 (1.078 g, 1.29 mmol) was performed according to the procedure described in experiment 26. The crude was purified by flash column chromatography on silica gel (20:80, EtOAc/Hex) affording the α (0.671 g, 66%) and the β-alcohol (0.286 g, 28%) as viscous colourless gums.

TBAF (1M in THF; 0.83 mL, 0.83 mmol) was added to a solution of the α-galactoside (0.655 g, 0.83 mmol) in THF (4 mL) at r.t. The reaction mixture was stirred for 4 hours and then water was added. The mixture was extracted with EtOAc, dried (MgSO$_4$) and concentrated to give a yellow viscous residue. Purification by flash column chromatography on silica gel (80:20, EtOAc/hexane) afforded the α-diol as a viscous colourless gum (0.467 g, 92%). After catalytic hydrogenation of the benzyl ethers from the α-diol (0.140 g, 1.50 mmol) and hydrolysis of the methyl ester according to the procedure described in experiment 26, the compound 146 was obtained as a viscous colorless foam (0.416 g, quantitative). Alpha product 146: [α]$^{20}_D$=+127.6 (c=0.62, H$_2$O). $^1$H NMR (D$_2$O): δ 4.97 (d, J=3.9 Hz, 1H, H-1), 4.13 (dt, J=4.7 Hz, J=2.3 Hz, 1H, CHCH$_2$OH), 3.99 (t, J=6.2 Hz, 1H), 3.93-3.87 (m, 2H), 3.81 (dd, J=12.1, 3.2 Hz, 1H), 3.77-3.70 (m, 2H), 3.69-3.64 (m, 2H, H-6, H'-6) ppm. $^{13}$C NMR (D$_2$O): δ 177.1 (CHCO$_2^-$), 97.6 (C-1), 79.2 (CHCH$_2$OH), 71.3, 69.6, 69.3, 68.5, 63.1 (CHCH$_2$OH), 61.2 (C-6) ppm.

The same strategy was applied for the deprotection of the β-galactoside (0.266 g, 0.34 mmol). After fluorolysis (0.140 g, 76%), catalytic hydrogenation of the benzyl ethers from the β-diol (0.340 g, 0.615 mmol) and hydrolysis of the methyl ester, the compound 147 was obtained as a viscous colorless foam (0.188 g, quantitative). Beta product 147: $^1$H NMR (D$_2$O): δ 4.42 (d, J=7.5 Hz, 1H, H-1), 4.11 (dd, J=6.5 Hz, J=3.2 Hz, 1H, CHCH$_2$OH), 3.83-3.77 (m, 2H), 3.73-3.67 (m, 2H), 3.64-3.53 (m, 4H) ppm. $^{13}$C NMR (D$_2$O): δ 177.9 (CHCO$_2^-$), 102.6 (C-1), 81.3 (CHCH$_2$OH), 75.1, 72.6, 70.9, 68.7, 62.6 (CHCH$_2$OH), 60.9 (C-6) ppm.

Experiment 31. Synthesis of Potassium 3-O-(α-D-glucopyranosyl)-3-hydroxybutyrate (148)

The methanolysis of the acetate group of the glucoside 136 (0.823 g, 1.36 mmol) was performed according to the procedure described in experiment 26. The crude was purified by flash column chromatography on silica gel (40:60, EtOAc/Hex) affording the α (0.594 g, 82%) and the β-alcohol (0.066 g, 9%) as viscous colourless gums.

After catalytic hydrogenation of the benzyl ethers of the α-alcohol (0.516 g, 0.94 mmol) and hydrolysis of the methyl ester according to the procedure described in experiment 26, the compound 148 was obtained as a viscous colorless foam (0.285 g, quantitative). $^1$H NMR (D$_2$O): δ 4.98 (d, J=4.0 Hz, H-1), 4.97 (d, J=4.2 Hz, H-1), 4.14-4.04 (m, CHCH$_3$), 3.80-3.59 (m), 3.45-3.39 (m, H-2), 3.34-3.28 (m, H-4), 2.47 (dd, J=14.2 Hz, J=6.9 Hz, CHCH$_2$CO$_2^-$), 2.40-2.22 (m, CHCH$_2$CO$_2^-$), 1.21 (d, J=6.1 Hz, CHCH$_3$), 1.14 (d, J=5.9 Hz, CHCH$_3$) ppm. $^{13}$C NMR (D$_2$O): δ 180.19, 180.16, 97.6 (C-1), 94.9 (C-1), 73.4 (CHCH$_3$), 73.15 (CHCH$_3$), 73.06, 71.9, 71.51, 71.48, 71.32, 70.5, 69.62, 69.56, 60.6 (C-6), 60.3 (C-6), 45.6 (CHCH$_2$CO$_2^-$), 44.5 (CHCH$_2$CO$_2^-$), 20.6 (CHCH$_3$), 18.0 (CHCH$_3$) ppm.

Experiment 32. Synthesis of Potassium 3-O-(α/β-D-galactopyranosyl)-3-hydroxybutyrate (149)

The methanolysis of the acetate group of the galactoside 137 (0.709 g, 1.17 mmol) was performed according to the procedure described in experiment 26. The crude was purified by flash column chromatography on silica gel (40:60, EtOAc/Hex) affording the alcohol as a viscous colourless gum (0.584 g, 88%, α/β=3:1). After catalytic hydrogenation of the benzyl ethers (0.573 g, 1.01 mmol) and hydrolysis of the methyl ester according to the procedure described in experiment 26, the compound 145 was obtained as a viscous colorless foam (0.309 g, quantitative, α/β=3:1). $^1$H NMR (D$_2$O): δ 5.01 (d, J=3.9 Hz, H-1 (α)), 4.99 (d, J=3.8 Hz, H-1 (α)), 4.42 (d, J=8.4 Hz, H-1 (β)), 4.40 (d, J=8.1 Hz, H-1 (β)), 4.23-4.04 (m), 3.97-3.89 (m), 3.84 (t, J=3.9 Hz), 3.78-3.54 (m), 3.40 (dd, J=9.6, 8.2 Hz), 2.54-2.44 (m), 2.40-2.22 (m), 1.22-1.13 (m) ppm. $^{13}$C NMR (D$_2$O): δ 180.3, 179.9, 101.9 (C-1 (β)), 101.1 (C-1 (β)), 97.9 (C-1 (α)), 95.1 (C-1 (α)), 75.14, 75.10, 74.99, 74.0, 73.4, 72.79, 72.65, 71.02, 71.01, 70.8, 70.52, 70.44, 69.58, 69.46, 69.30, 69.1, 68.72, 68.56, 68.46, 68.2, 68.72, 68.56, 68.46, 68.2, 61.23, 61.09, 60.9, 45.75 (CH$\underline{C}$H$_2$CO$_2^-$), 45.57 (CH$\underline{C}$H$_2$CO$_2^-$), 44.5 (CH$\underline{C}$H$_2$CO$_2^-$), 20.6 (CH$\underline{C}$H$_3$), 19.3 (CH$\underline{C}$H$_3$), 18.0 (CH$\underline{C}$H$_3$) ppm.

Experiment 33. Synthesis of Potassium (2S)-2-O-(α/β-D-glucopyranosyl)-2-hydroxysuccinate (150)

The methanolysis of the acetate group of the glucoside 138 (0.263 g, 0.41 mmol) was performed according to the procedure described in experiment 26. The crude was purified by preparative TLC (50:50, EtOAc/Hex) affording the desired alcohol (0.117 g, 48%) as a viscous colourless gum, and recovery of the initial 138 (0.068 g, 26%) and the product of the hydrolysis at the anomeric position (0.046 g, 25%). After catalytic hydrogenation of the benzyl ethers (0.565 g, 0.95 mmol) and hydrolysis of the methyl ester according to the procedure described in experiment 26, the compound 145 was obtained as a viscous colorless foam (0.290 g, 94%). $^1$H NMR (D$_2$O): δ 4.94 (d, J=3.9 Hz, H-1 (α)), 4.39 (d, J=7.9 Hz, H-1 (β)), 4.19 (dd, J=10.4, J=3.1 Hz, 1H, CO$_2^-$C$\underline{H}$CH$_2$CO$_2^-$), 3.80-3.63 (m), 3.45-3.28 (m), 3.21-3.15 (m), 2.59 (dd, J=15.1 Hz, J=2.9 Hz, CHC$\underline{H}_2$CO$_2^-$ (β)), 2.52 (dd, J=15.2 Hz, J=3.2 Hz, CHC$\underline{H}_2$CO$_2^-$ (α)), 2.42 (dd, J=15.2 Hz, J=10.4 Hz, CHC$\underline{H}_2$CO$_2^-$ (α)) ppm. $^{13}$C NMR (D$_2$O): δ 179.5, 179.1, 135.3 (C-1 (β)), 99.7 (C-1 (α)), 95.9, 79.0, 75.92, 75.72, 74.1, 73.1, 72.2, 71.8, 71.4, 69.6, 69.2, 60.7, 60.0, 41.5 ppm.

Experiment 34. Synthesis of Potassium (2S)-2-O-(α/β-D-galactopyranosyl)-2-hydroxysuccinate 151, 152)

The methanolysis of the acetate group of the galactoside 139 (1.215 g, 1.91 mmol) was performed according to the procedure described in experiment 26. The crude was purified by flash column chromatography on silica gel (50:50, EtOAc/Hex) affording the α (0.642 g, 57%) and β-alcohol (0.176 g, 16%) as viscous colourless gums, and recovery of the starting material 139 (0.020 g, 16%) and the product of the hydrolysis at the anomeric position (0.067 g, 8%). After catalytic hydrogenation of the benzyl ethers from the α (0.640 g, 1.07 mmol) and β-alcohol (0.159 g, 0.27 mmol) and hydrolysis of the methyl ester according to the procedure described in experiment 26, the compounds 151 (0.401 g, quantitative) and 152 (0.100 g, quantitative) were obtained as viscous colorless foams. Alpha product 151: FTIR (film) v$_{max}$: 1634 (C=O), 3332 (O—H) cm$^-$. $^1$H NMR (D$_2$O): δ 4.96 (d, J=4.0 Hz, 1H, H-1) 4.20 (dd, J=10.3, 3.1 Hz, CO$_2^-$C$\underline{H}$CH$_2$CO$_2^-$), 4.05-4.02 (m), 3.94 (d, J=2.8 Hz), 3.86 (dd, J=10.4 Hz, J=3.3 Hz), 3.70-3.54 (m), 2.54 (dd, J=15.2 Hz, 3.2 Hz, 1H, CHC$\underline{H}_2$CO$_2^-$), 2.43 2.42 (dd, J=15.2 Hz, J=10.3 Hz, 1H, CHC$\underline{H}_2$CO$_2^-$) ppm. Beta product 152: FTIR (film) v$_{max}$: 1736 (C=O), 3410 (O—H) cm$^{-1}$. $^1$H NMR (D$_2$O): δ 4.52 (dd, J=10.0 Hz, J=3.1 Hz, 1H, CO$_2^-$C$\underline{H}$CH$_2$CO$_2^-$), 4.33 (d, J=7.5 Hz, 1H, H-1), 3.83-3.82 (m, 1H), 3.77-3.50 (m, 5H), 2.62 (dd, J=15.2, 3.1 Hz, 1H, CHC$\underline{H}_2$CO$_2^-$), 2.44 (dd, J=15.2, 10.0 Hz, 0.1H, CHC$\underline{H}_2$CO$_2^-$). $^{13}$C NMR (D$_2$O): δ 179.4 (CO$_2^-$), 179.0 (CO$_2^-$), 102.0 (C-1), 77.6 ($\underline{C}$HCH$_2$CO$_2^-$), 75.4, 72.8, 70.9, 68.8, 61.3 (C-6), 41.9 (CH$\underline{C}$H$_2$CO$_2^-$) ppm.

Experiment 35. Synthesis of Potassium (2S)-2-O-(α-D-glucopyranosyl)-2,3-dihydroxypropanoate (153)

The methanolysis of the acetate group of the glucoside 140 (0.450 g, 0.54 mmol) was performed according to the procedure described in experiment 26. The crude was purified by flash column chromatography on silica gel (20:80, EtOAc/Hex) affording the α (0.299 g, 70%) and the β-alcohol (0.030 g, 7%) as viscous colourless gums.

TBAF (1M in THF; 0.37 mL, 0.37 mmol) was added to a solution of the α-glucoside (0.290 g, 0.37 mmol) in THF (2 mL) at r.t. The reaction mixture was stirred for 4 hours and then water was added. The mixture was extracted with EtOAc, dried (MgSO$_4$) and concentrated to give a yellow viscous residue. Purification by flash column chromatography on silica gel (80:20, EtOAc/hexane) afforded the α-diol as a viscous colourless gum (0.162 g, 80%). After catalytic hydrogenation of the benzyl ethers from the α-diol (0.150 g, 0.27 mmol) and hydrolysis of the methyl ester according to the procedure described in experiment 26, the compound 153 was obtained as a viscous colorless foam (0.077 g, quantitative). $^1$H NMR (D$_2$O): δ 4.96 (d, J=3.9 Hz, 1H, H-1), 3.96 (dd, J=3.3 Hz, J=6.5 Hz, 1H, C$\underline{H}$CH$_2$OH), 3.79-3.75 (m, 3H), 3.72-3.63 (m, 3H), 3.48 (dd, J=3.9 Hz, J=9.9 Hz, 1H, H-2), 3.37 (t, J=9.6 Hz, 1H, H-4) ppm. $^{13}$C NMR (D$_2$O): δ 177.4 (CO$_2^-$), 99.2 (C-1), 81.4 ($\underline{C}$HCH$_2$OH), 72.9, 72.2, 71.7 (C-2), 69.3 (C-4), 62.6 (CH$\underline{C}$H$_2$OH), 60.0 (C-6) ppm.

Experiment 36. Synthesis of Potassium (2S)-2-O-(α-D-galactopyranosyl)-2,3-dihydroxypropanoate (154)

The methanolysis of the acetate group of the α-galactoside 141 (0.640 g, 0.77 mmol) was performed according to the procedure described in experiment 26. The crude was purified by flash column chromatography on silica gel (30:70, EtOAc/Hex) affording the alcohol (0.572 g, 94%) as a viscous colourless residue.

TBAF (1M in THF; 0.83 mL, 0.88 mmol) was added to a solution of the α-galactoside (0.695 g, 0.88 mmol) in THF (5 mL) at r.t. The reaction mixture was stirred for 4 hours and then water was added. The mixture was extracted with EtOAc, dried (MgSO$_4$) and concentrated to give a yellow viscous residue. Purification by flash column chromatography on silica gel (80:20, EtOAc/hexane) afforded the diol as a viscous colourless gum (0.343 g, 71%). After catalytic hydrogenation of the benzyl ethers from the diol (0.310 g, 0.56 mmol) and hydrolysis of the methyl ester according to the procedure described in experiment 26, the compound 154 was obtained as a viscous colorless foam (0.172 g, quantitative). $^1$H NMR (D$_2$O): δ 5.01 (d, J=3.9 Hz, 1H, H-1), 4.28 (t, J=4.2 Hz, 1H, C$\underline{H}$CH$_2$OH), 4.18-3.92 (m, 4H), 3.85-3.58 (m, 4H) ppm.

Experiment 37. Synthesis of Potassium (2S)-2-O-(β-D-galactopyranosyl)-2,3-dihydroxypropanoate (155)

The methanolysis of the acetate group of the β-galactoside 141 (0.275 g, 0.33 mmol) was performed according to the procedure described in experiment 26. The crude was purified by flash column chromatography on silica gel (40:60, EtOAc/Hex) affording the alcohol (0.243 g, 93%) as a viscous colourless residue.

TBAF (1M in THF; 0.83 mL, 0.44 mmol) was added to a solution of the β-galactoside (0.350 g, 0.44 mmol) in THF (3 mL) at r.t. The reaction mixture was stirred for 4 hours and then water was added. The mixture was extracted with EtOAc, dried (MgSO$_4$) and concentrated to give a yellow viscous residue. Purification by flash column chromatography on silica gel (80:20, EtOAc/hexane) afforded the diol as a viscous colourless gum (0.151 g, 62%). After catalytic hydrogenation of the benzyl ethers from the diol (0.140 g, 0.25 mmol) and hydrolysis of the methyl ester according to the procedure described in experiment 26, the compound 155 was obtained as a viscous colorless foam (0.078 g, quantitative). $^1$H NMR (D$_2$O): δ 4.38 (d, J=7.4 Hz, 1H, H-1), 4.28 (dd, J=6.2 Hz, J=2.9 Hz, 1H, C$\underline{\text{H}}$CH$_2$OH), 3.84 (dt, J=7.2, 3.8 Hz, 2H), 3.76-3.68 (m, 3H), 3.66-3.53 (m, 4H) ppm. $^{13}$C NMR (D$_2$O): δ 177.1 (CO$_2^-$), 102.5 (C-1), 81.4 ($\underline{\text{C}}$HCH$_2$OH), 75.3, 72.8, 71.0, 68.6, 63.2 (CHCH$_2$OH), 61.0 (C-6) ppm.

Experiment 38. Synthesis of Ethyl 3-O-(2,3,4,6-tetra-O-acetyl-α-D-mannopyranosyl)-3-hydroxybutyrate (156)

Ethyl 3-dihydroxybutyrate (0.348 mL, 2.68 mmol) was added to a solution of trichloroacetamidate 103 (1.100 g, 2.23 mmol) in dry CH$_2$Cl$_2$ (6 mL). The solution was cooled to 0° C. and BF$_3$OEt$_2$ (0.0.282 mL, 2.23 mmol) was slowly added. When the reaction was completed, a saturated aqueous solution of NaHCO$_3$ was added, followed by extractions with C$\underline{\text{H}}_2$Cl$_2$ (3×15 mL). The combined organic phases were dried (MgSO$_4$) and concentrated. The residue was purified by flash column chromatography on silica gel (40:60, EtOAc/hexane) to afford 156 (0.943 g, 91%) as a viscous colourless residue.

Experiment 39. Synthesis of Dimethyl (2S)-2-O-(2,3,4,6-tetra-O-acetyl-α-D-mannopyranosyl)-2-hydroxysuccinate (157)

The glycosylation reaction of trichloroacetamidate donor 103 (1.540 g, 3.12 mmol) and ethyl dimethyl dimethyl (S)-malate 134 (0.494 mL, 3.75 mmol) was performed according to the procedure described in experiment 38. The crude was purified by flash column chromatography on silica gel (30:70, EtOAc/Hex) affording the product 157 as a viscous colourless gum (1.359 g, 88%).

Experiment 40. Synthesis of Methyl 3-O-tert-butyldimethylsilyl-(2S)-2-O-(2,3,4,6-tetra-O-acetyl-α-D-mannopyranosyl)-2,3-dihydroxypropanoate (158)

The glycosylation reaction of trichloroacetamidate donor 103 (1.30 g, 2.64 mmol) and acceptor 135 (0.946 g, 2.64 mmol) was performed according to the procedure described in experiment 38. The crude was purified by flash column chromatography on silica gel (30:70, EtOAc/Hex) affording the product 158 as a viscous colourless gum (1.33 g, 73%).

Experiment 41. Synthesis of Potassium 3-O-(α-D-mannopyranosyl)-3-hydroxybutyrate (159)

A solution of NaOMe 1N (0.36 mL, 0.36 mmol) in MeOH was added to a stirred solution of 156 (0.276 g, 0.60 mmol) in MeOH (3 mL) at 0° C. After complete conversion of the starting material, previously activated Dowex-H$^+$ resin was added until neutral pH. After filtration with MeOH and water, the solvent was removed in vacuum to yield the deprotected mannoside as a viscous colourless gum (0.157 g, 90%).
A solution of 2 M KOH (0.78 mL) was added to a stirred solution of the previously mannoside (0.431 g, 1.56 mmol) in H$_2$O (4 mL). After all of the starting material had been consumed, the pH was adjusted to 7 with 10% HCl and the solvent was evaporated to afford 159 as a viscous colorless foam (0.446 g, quantitative). $^1$H NMR (D$_2$O): δ 4.91 (d, J=7.5 Hz), 4.18-4.09 (m, (C$\underline{\text{H}}$CH$_3$), 3.84-3.77 (m), 3.74-3.63 (m), 3.57 (t, J=8.9 Hz), 2.43-2.21 (m, (CHC$\underline{\text{H}}_2$CO$_2^-$)), 1.20 (d, J=6.1 Hz, CHC$\underline{\text{H}}_2$CO$_2^-$), 1.14 (d, J=5.6 Hz, CHC$\underline{\text{H}}_2$CO$_2^-$) ppm. $^{13}$C NMR (CDCl$_3$): δ 179.9 (CH$_2$$\underline{\text{C}}$O$_2^-$), 179.8 (CH$_2$$\underline{\text{C}}$O$_2^-$), 99.7 (C-1), 96.5 (C-1), 73.4, 72.9, 72.5, 70.57, 70.52, 70.41, 70.29, 70.24, 66.84, 66.72, 61.0 (C-6), 60.7 (C-6), 45.5 (CHC$\underline{\text{H}}_2$CO$_2^-$), 44.8 (CHC$\underline{\text{H}}_2$CO$_2^-$), 20.8 (CHC$\underline{\text{H}}_3$) ppm.

Experiment 42. Synthesis of Potassium (2S)-2-O-(α-D-mannopyranosyl)-2-hydroxysuccinate (160)

The methanolysis of the acetate groups of the mannoside 157 (1.343 g, 2.72 mmol) was performed according to the procedure described in experiment 41. The crude was purified by column chromatography on silica gel (20:80, MeOH/CH$_2$Cl$_2$) affording the desired deprotected mannoside (0.685 g, 78%) as a viscous colourless gum, and the product of the hydrolysis at the anomeric position, the D-mannopyranoside (0.100 g, 20%). After hydrolysis of the methyl ester according to the procedure described in experiment 38 compound 160 was obtained as a viscous colorless foam (0.0.786 g, quantitative). $^1$H NMR (D$_2$O): δ 4.85 (t, J=15.6 Hz, 1H), 4.85 (s, 1H, H-1), 4.24 (dd, J=8.2 Hz, J=4.7 Hz, 1H), 3.90-3.58 (m, 5H), 2.79-2.64 (m, 2H) ppm.

Experiment 43. Synthesis of Potassium (2S)-2-O-(D-mannopyranosyl)-2,3-dihydroxypropanoate (161)

TBAF (1M in THF; 0.38 mL, 0.38 mmol) was added to a solution of the 158 (0.220 g, 0.32 mmol) in THF (3 mL) at r.t. The reaction mixture was stirred for 4 hours and then water was added. The mixture was extracted with EtOAc, dried (MgSO$_4$) and concentrated to give a yellow viscous residue. Purification by preparative TLC (60:40, EtOAc/hexane) afforded the alcohol as a viscous colourless gum (0.103 g, 72%). The methanolysis of the acetate groups of the alcohol (0.518 g, 1.15 mmol) was performed according to the procedure described in experiment 41. After complete conversion of the starting material, previously activated Dowex-H$^+$ resin was added until neutral pH. After filtration with MeOH and water, the solvent was removed in vacuum to yield the deprotected mannoside as a viscous colourless gum (0.312 g, 96%). Hydrolysis of the methyl ester according to the procedure described in experiment 41, the compound 161 was obtained as a viscous colorless foam (0.300 g, quantitative). $^1$H NMR (D$_2$O): δ 4.89 (d, J=1.4 Hz, 1H, H-1), 4.02 (dd, J=7.1, 3.2 Hz, 1H, C$\underline{\text{H}}$CO$_2^-$), 3.99 (dd, J=3.4, 1.6 Hz, 1H, H—), 3.89 (dd, J=9.5, 3.4 Hz, 1H), 3.79 (dd, J=12.2, 3.1 Hz, 1H, H—), 3.74-3.61 (m, 5H) ppm. $^{13}$C NMR (CDCl$_3$): δ 100.8, 80.6 (C-1), 73.2, 70.5, 70.1, 66.5, 62.5, 60.5 ppm.

Experiment 44. Synthesis of Dimethyl (2S)-2-O-(2-azido-3,4,di-O-benzyl-6-O-chloroacetyl-2-deoxy-α-D-glucopyranosyl)-2-hydroxysuccinate (162)

A suspension of thioglucoside donor 91 (0.750 g, 1.32 mmol), methyl (S)-malate 134 (0.197 mL, 1.52 mmol) and 4 Å MS in CH$_2$Cl$_2$:Et$_2$O (1:4, 20 mL) was stirred for 1 h at room temperature then cooled to 0° C. A solution of N-iodosuccinimide (0.0594 g, 2.64 mmol) and TfOH (0.027 mL) in C$\underline{\text{H}}_2$Cl$_2$:Et$_2$O (1:1, 20 mL) was added at 0° C. After complete conversion of the starting material, 10% Na$_2$S$_2$O$_3$ aqueous solution (20 mL) and saturated aqueous NaHCO$_3$ solution (10 mL) were added. The mixture was extracted with CH$_2$Cl$_2$ (3×20 mL), the combined organic phases were dried (MgSO$_4$), filtered and the solvent was removed under vacuum. The crude product was purified by flash column chromatography on silica gel (30:70, EtOAc/Hex) to afforded product 162 as a viscous colourless foam (0.672 g, 84%).

Experiment 45. Synthesis of Methyl (2S)-2-(2-azido-3,4, di-O-benzyl-2-deoxy-α-D-glucopyranosyl) propanoate (163)

A solution of NaOMe 1N (0.46 mL, 0.46 mmol) in MeOH was added to a stirred solution of 95 (0.470 g, 0.77 mmol) in MeOH (5 mL) at 0° C. After 1 hour the reaction mixture was neutralized with saturated aqueous NH$_4$Cl. The aqueous phase was extracted with EtOAc and the combined organic extracts were dried (MgSO$_4$), filtered and the solvent was removed. The crude product was purified by flash column chromatography on silica gel (30:70, EtOAc/Hex) to afford 163 (0.355 g, 98%) as a viscous colourless gum.

Experiment 46. Synthesis of Methyl 2-(2-azido-3,4, di-O-benzyl-2-deoxy-α-D-glucopyranosyl)acetate (164)

The procedure of experiment 45 was applied to compound 96 (0.500 g, 0.94 mmol) affording compound 164 as a viscous colourless gum (0.393 g, 92%).

Experiment 47. Synthesis of Methyl (2R)-tert-butyldimethylsilyl-3-(2-azido-3,4,di-O-benzyl-2-deoxy-α-D-glucopyranosyl)-2,3-dihydroxyropanoate (165)

TBAF (1M in THF; 1.14 mL, 1.14 mmol) was added to a solution of 97 (0.830 g, 1.03 mmol) in THF (7 mL) at r.t. The reaction mixture was stirred for 4 hours and then water was added. The mixture was extracted with EtOAc, dried (MgSO$_4$) and concentrated to give a yellow viscous residue. Purification by flash column chromatography on silica gel (50:50, EtOAc/hexane) afforded the alcohol as a viscous colourless gum (0.401 g, 72%). The procedure of experiment 45 was applied to the alcohol (0.296 g, 0.55 mmol) affording 165 as a viscous colourless gum (0.261 g, 92%).

Experiment 48. Synthesis of Dimethyl (2S)-2-O-(2-azido-3,4,di-O-benzyl-2-deoxy-α-D-glucopyranosyl)-2-hydroxysuccinate (166)

The procedure of experiment 45 was applied to compound 162 (0.670 g, 1.10 mmol) affording compound 166 as a viscous colourless gum (0.429 g, 73%).

Example 2: Protein Stabilizing Effects of the Compatible Solutes of Example 1 in Three Model Proteins The ability of the new synthetic analogues to stabilize three model proteins against thermal stress was assessed using differential scanning fluorimetry (DSF). In this study, malate dehydrogenase (MDH), staphylococcal nuclease (SNase) and lysozyme were used as model proteins, and the stabilising effect of the synthetic compounds was compared with the effect of natural solutes, like MG and GG as well as potassium chloride, and other previously synthesised non-natural solutes, like MGlyc and ML.

The compounds tested are shown in Tables 6 and 7.

TABLE 6

Chemical structures of the natural and synthetic glucose, galactose and mannose derivatives tested in this study.

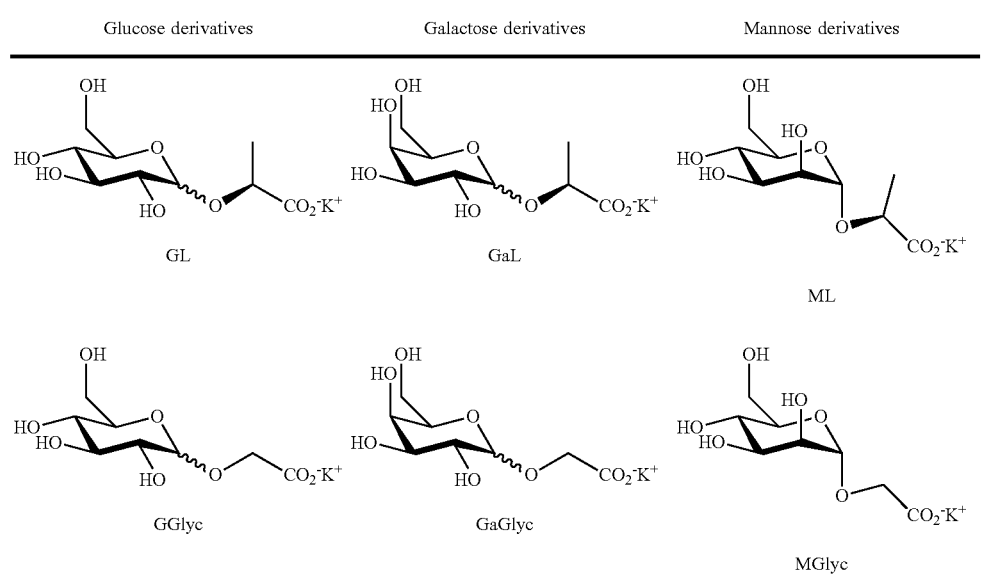

TABLE 6-continued
Chemical structures of the natural and synthetic glucose, galactose and mannose derivatives tested in this study.
| Glucose derivatives | Galactose derivatives | Mannose derivatives |
| --- | --- | --- |
| 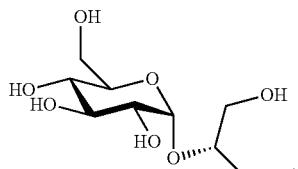<br>GG (D) | 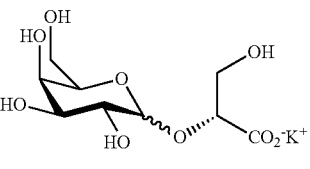<br>GaG (α, D)<br>GaG (β, D) | 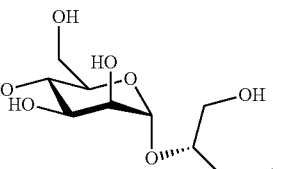<br>MG (D) |
| 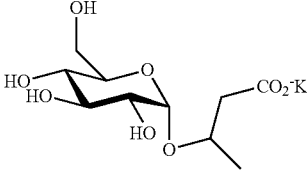<br>GBut | 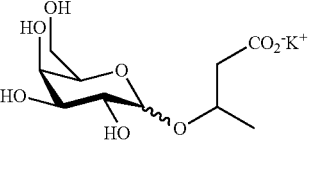<br>GaBut | 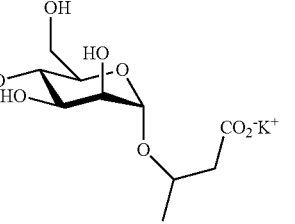<br>MBut |
| 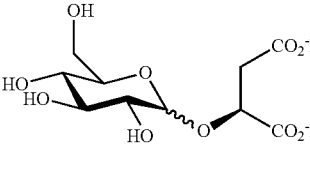<br>GMal | 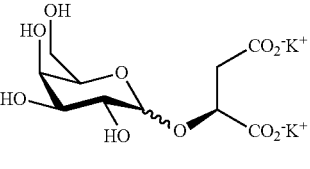<br>GaMal (α)<br>GaMal (β) | 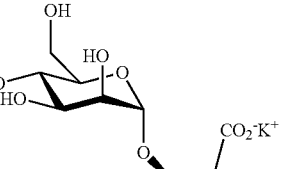<br>MMal |
| 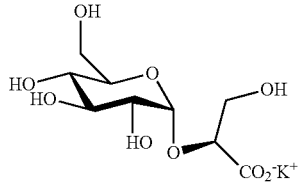<br>GG (L) | 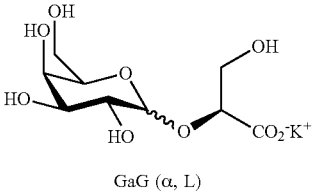<br>GaG (α, L)<br>GaG (β, L) | 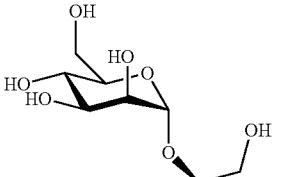<br>MG (L) |

TABLE 7

Chemical structures of the synthetic glucosamine and N-acetyl glucosamine derivatives tested in this study.

| Glucosamine derivatives | N-Acetyl Glucosamine derivatives |
|---|---|

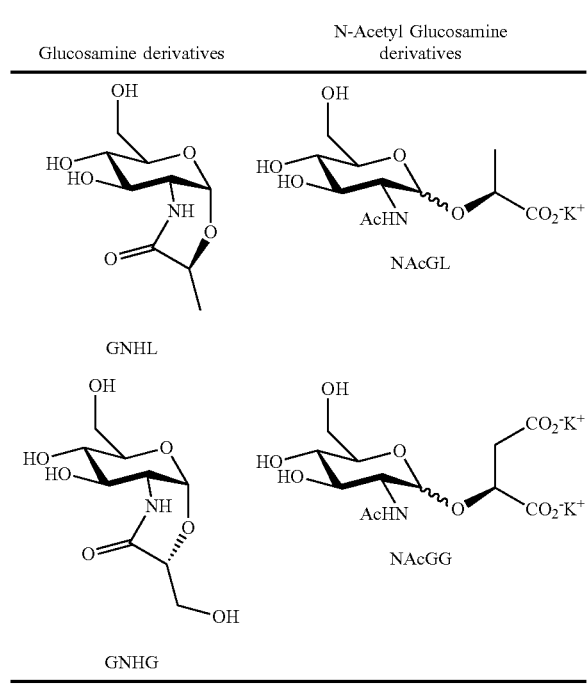

GNHL, NAcGL, GNHG, NAcGG

The DSF based stability assays were performed at each protein working pH and the melting temperatures ($T_M$) values determined in the absence (control experiments) and in the presence of solutes, and at different solute concentrations. The denaturation curves for each assay were analysed, and the melting temperatures determined by the calculation of the first derivative, which corresponds to the midpoint temperature of the protein-unfolding transition. In the absence of solutes, malate dehydrogenase (MDH), staphylococcal nuclease (SNase) and lysozyme have melting temperatures ($T_M$) of 50, 52 and 71° C. respectively. The unfolding temperature shifts ($\Delta T_M$) were calculated by comparing the $T_M$ values obtained in the presence of solutes with the $T_M$ values of the control experiments (absence of solutes). Positive $\Delta T_M$ values correspond to an increase in the $T_M$ meaning that the protein is more stable and more energy (heat) is needed to unfold it. Negative $\Delta T_M$ values correspond to a decrease in the $T_M$ meaning that the protein is less stable.

The increment in the melting temperature ($\Delta T_M$) of the three enzymes induced by the presence of the synthetic and the natural solutes is depicted in FIG. 1.

Figure 2:
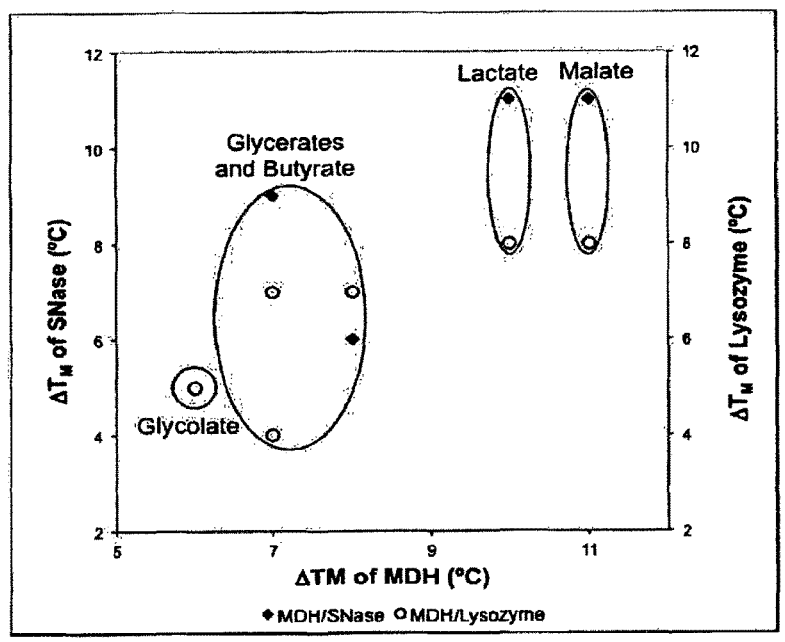
FIG. 2: Stabilising effect of different glucose derivatives against thermal denaturation of malate dehydrogenase (MDH), staphylococcal nuclease (SNase) and lysozyme. In the abscissa axis the increment in the melting temperature of MDH induced by 0.5 M of several compounds, and in the ordinates axis the increment in the melting temperature of SNase (solid symbols) and Lysozyme (open symbols) are plotted.
Figure 3:
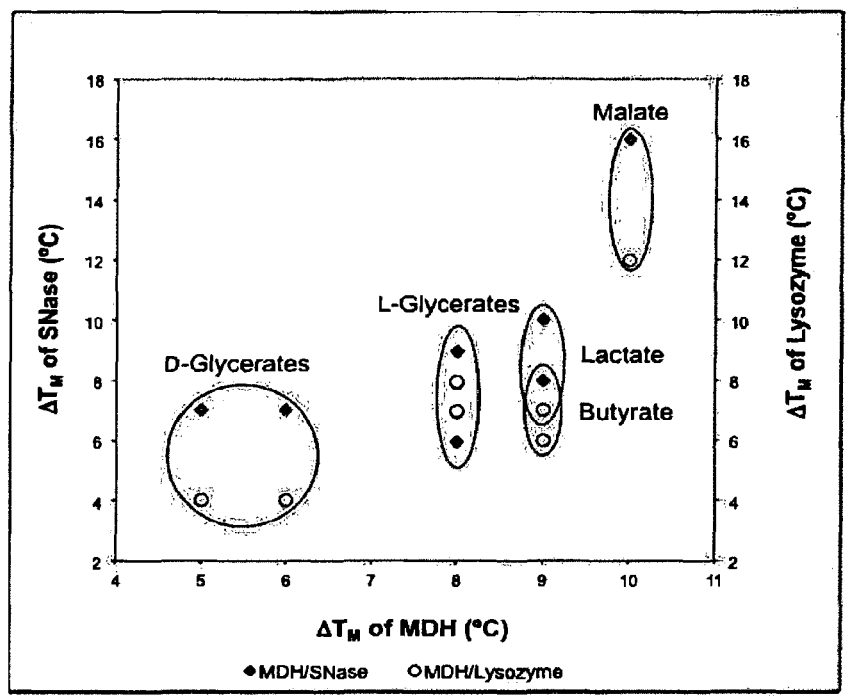
FIG. 3: Stabilising effect of different galactose derivatives against thermal denaturation of malate dehydrogenase (MDH), staphylococcal nuclease (SNase) and lysozyme. In the abscissa axis the increment in the melting temperature of MDH induced by 0.5 M of several compounds, and in the ordinates axis the increment in the melting temperature of SNase (solid symbols) and Lysozyme (open symbols) are plotted.

Analysis of different glucose derivatives (FIG. 2) and galactose (FIG. 3) showed the importance of the non-glycosidic group attached do the hexose.

Figure 4:
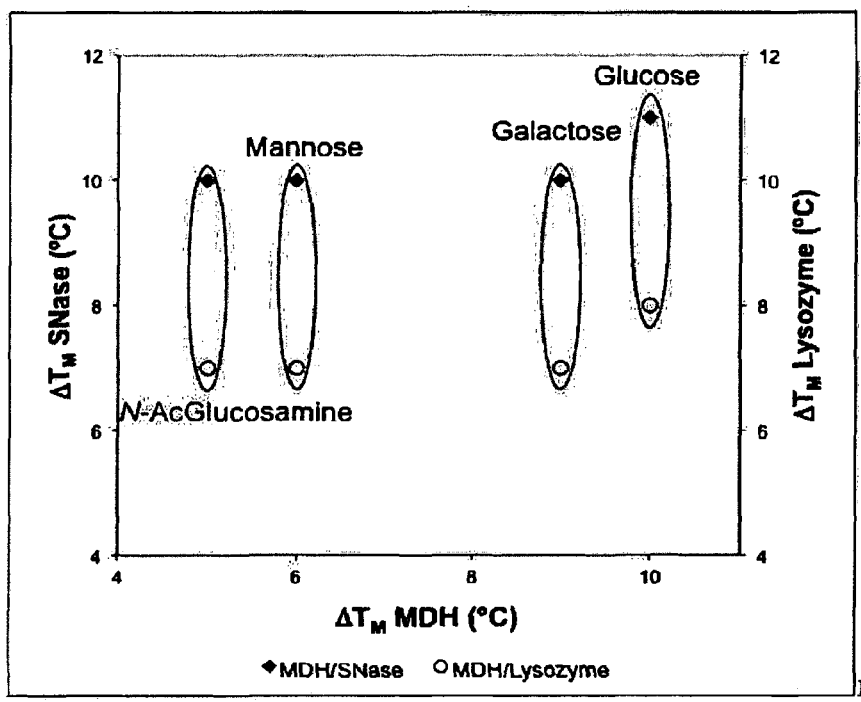
FIG. 4: Stabilising effect of different lactate derivatives against thermal denaturation of malate dehydrogenase (MDH), staphylococcal nuclease (SNase) and lysozyme. In the abscissa axis the increment in the melting temperature of MDH induced by 0.5 M of several compounds, and in the ordinates axis the increment in the melting temperature of SNase (solid symbols) and Lysozyme (open symbols) are plotted.
Figure 5:
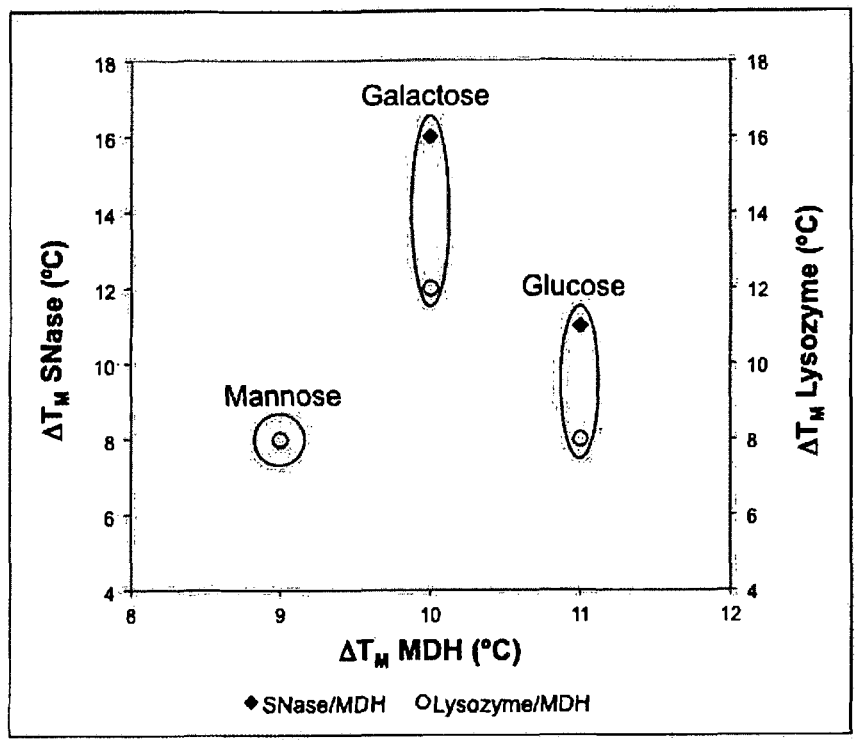
FIG. 5: Stabilising effect of different malate derivatives against thermal denaturation of malate dehydrogenase (MDH), staphylococcal nuclease (SNase) and lysozyme. In the abscissa axis the increment in the melting temperature of MDH induced by 0.5 M of several compounds, and in the ordinates axis the increment in the melting temperature of SNase (solid symbols) and Lysozyme (open symbols) are plotted.

Concerning the importance of the sugar structure different lactate (FIG. 4) and malate derivatives (FIG. 5) were analysed.

When plotting the increment of the melting temperature of MDH versus those of SNase and lysozyme (FIGS. 2-5), a general view of the results arises.

General conclusions for the tested proteins:
charged compounds are better stabilisers;
malate (the best) and lactate derivatives give higher stabilization;
the non-sugar moiety has greater influence in the stabilisation effect than the hexose structure; and glucose and galactose derivatives are better stabilisers.

Figure 6:
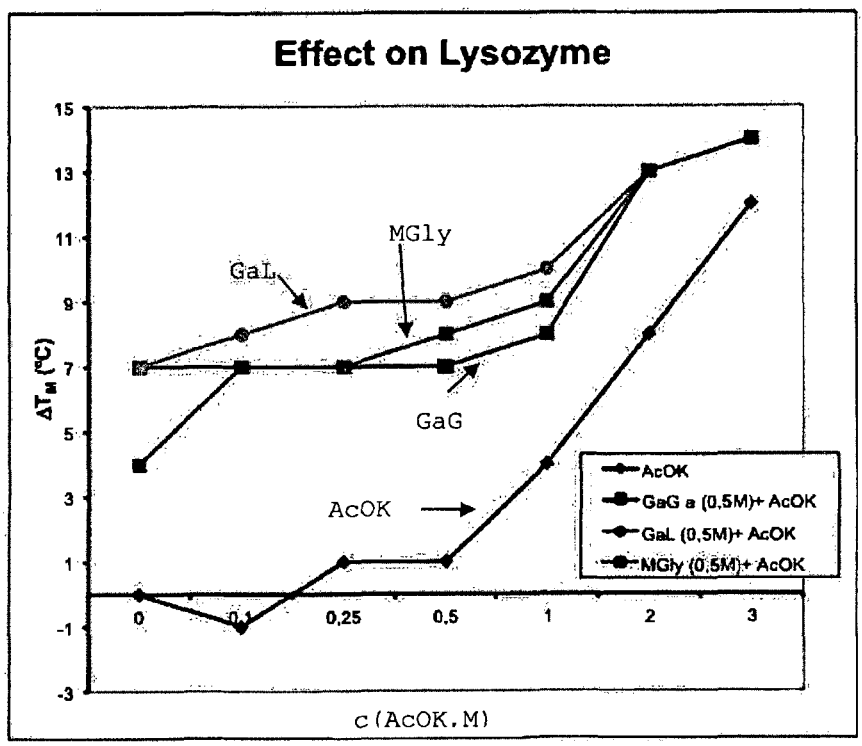
FIG. 6: Stabilising effect dependence on concentration of AcOK alone and in conjugation with different hypersolutes (0.5M).

The stabilising effect of potassium acetate salt (AcOK) on lysozyme was studied in conjugation with the hypersolutes (FIG. 6). The results showed that alone AcOK is not a good stabiliser, stabilising only at high salt concentrations. However, in conjugation with the hypersolutes it is able to enhance their stabilisation properties.

Figure 7:
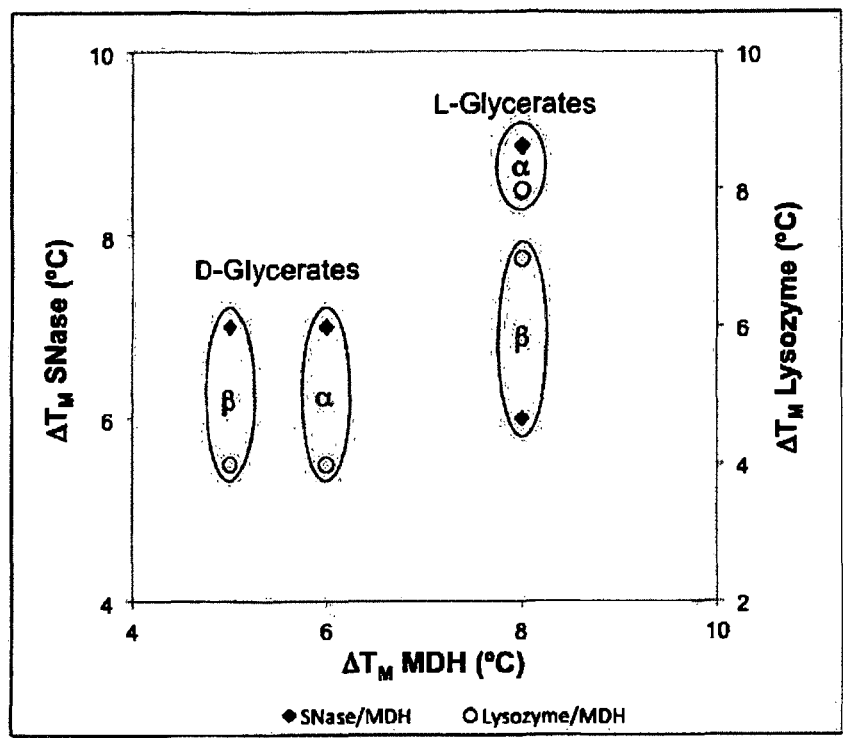
FIG. 7: Stabilising effect of different galactosyl glycerate derivatives against thermal denaturation of malate dehydrogenase (MDH), staphylococcal nuclease (SNase) and lysozyme. In the abscissa axis the increment in the melting temperature of MDH induced by 0.5 M of several compounds, and in the ordinate axis the increment in the melting temperature of SNase (solid symbols) and Lysozyme (open symbols) are plotted.

To determine the importance of the glycosidic linkage of the sugar for the stabilisation effect, different α and β anomers of D and L-galactosyl glycerates were studied (FIG. 7). Results obtained for the three enzymes showed that L-glycerates were better stabilisers than the natural D-glycerate derivatives, and that the β-anomers were better stabilisers than those with the β configuration.

Figure 8:
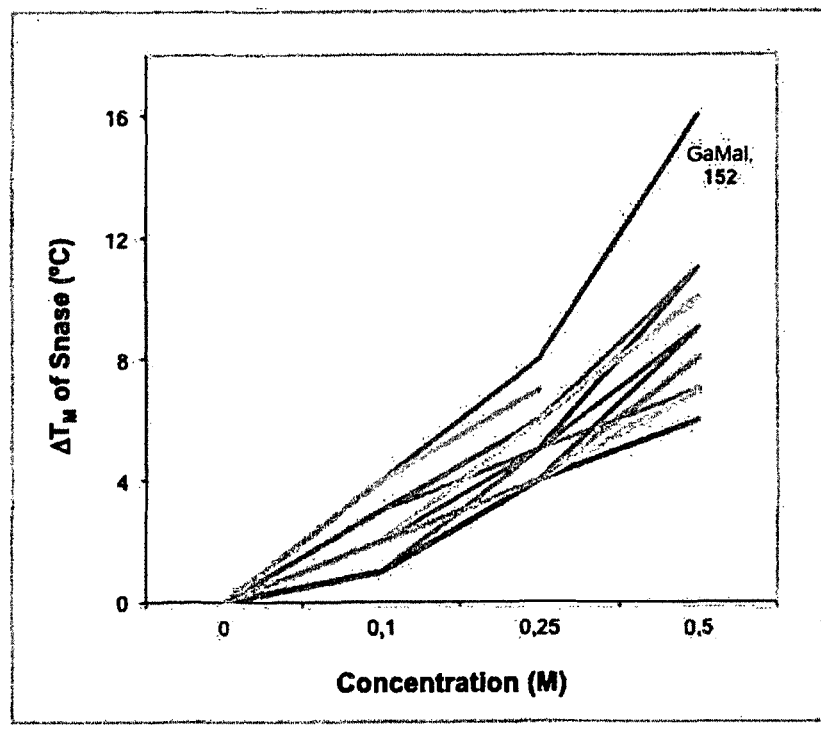
FIG. 8: Dependence of SNase melting temperature on the concentration of solutes.
Figure 9:
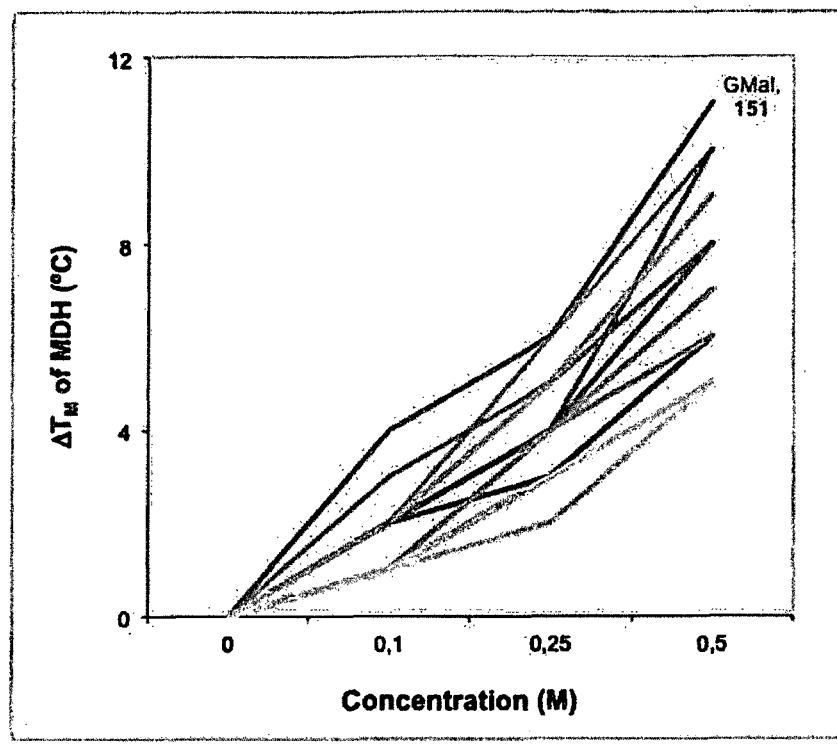
FIG. 9: Dependence of MDH melting temperature on the concentration of solutes.
Figure 10:
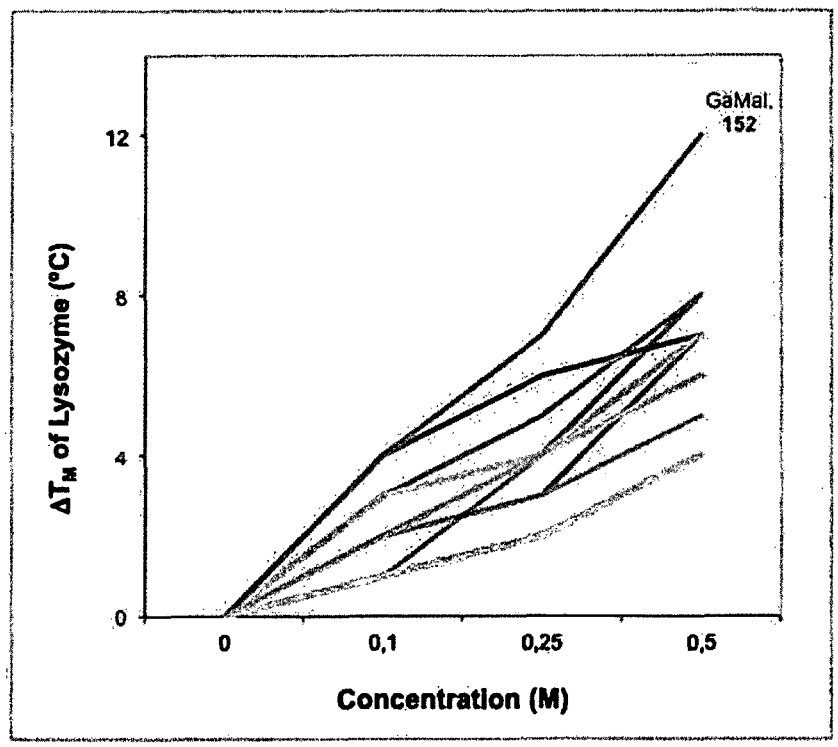
FIG. 10: Dependence of lysozyme melting temperature on the concentration of solutes.

In order to study the dependence of the increment of the melting temperature on the concentration of the solutes, the proteins were tested at different solute concentrations—0.1, 0.25 and 0.5 M (FIG. 8, FIG. 9, and FIG. 10). For the three proteins, results showed that independent of the degree of stabilisation, the stabilisation effect was directly proportional to the concentration of the solute. Although the results obtained seem to follow a general trend, when taking a closer look in the case of SNase (FIG. 8) and lysozyme (FIG. 10) α-galactosyl malate is clearly the best stabiliser. In the case of MDH the results show that glucosyl malate was the best stabiliser for this enzyme.

Materials

Mannosylglycerate (MG), glucosylglycerate (GG), glucosylglucosylglycerate (GGG), mannosyl glycolate (MGly) and mannosyl lactate (ML) were obtained by chemical synthesis as described in literature (Costa 1998). New synthetic compounds were obtained by chemical synthesis as described in Example 1. The desired compounds were purified by size exclusion chromatography on a Sephadex G-10 column eluted with water. The fractions containing the pure compounds were pooled, lyophilized. Purity and concentration of the compounds was assessed by $^1$H NMR spectra obtained at 500 MHz spectrometer in $D_2O$. For quantification purposes, spectra were acquired with a repetition delay of 60 s with formate as concentration standard. Only samples with purity higher than 98% were used. Mitochondrial malate dehydrogenase from pig heart (MDH) was purchased from Roche, and hen egg white lysozyme was purchased from Sigma-Aldrich. These enzymes were used without further purification. Recombinant staphylococcal nuclease A (SNase) was produced and purified from *Escherichia coli* cells as described by Faria 2008. Protein concentration was determined from UV absorbance at 280 nm, using 0.28 $(mg/mL)^{-1}$ $cm^{-1}$ for the extinction coefficient of MDH, 2.58 $(mg/mL)^{-1}$ $cm^{-1}$ for lysozyme and 0.93 $(mg/mL)^{-1}$ $cm^{-1}$ for SNase.

DSF Assay

The protein melting temperature ($T_M$) determination was performed by monitoring protein unfolding with the fluoroprobe SYPRO Orange dye (Molecular Probes), which although completely quenched in aqueous environment, emits fluorescence upon binding to protein hydrophobic patches. Such increase in fluorescence can be measured as a function of temperature using Differential Scanning Fluorimetry. In a typical assay with a total volume of 20 µL, a protein concentration from 0.14 to 0.21 mg/mL, and a dye concentration of 5 fold were used to guarantee the best signal to noise ratio. Protein stock solutions of SNase or MDH were prepared in phosphate buffer (20 mM of sodium phosphate, pH 7.6), and lysozyme was prepared in citrate buffer (40 mM sodium citrate, 110 mM NaCl, pH 6.0). These stock solutions were extensively dialyzed against the same buffer before the assays. Protein concentrations approximately 1.9 µM were used for MDH, 12.4 µM for SNase and 13 µM for lysozyme. Solute solutions were prepared in water with the respective concentrations. The assay was prepared by adding 2 µL of protein to 8 µL of dye buffer solution, and 10 µL of solute solution, all prepared in the protein purification buffer except for the solutes solutions. Fluorescence intensities versus temperature are used to calculate the protein melting temperature ($T_M$) by determining the first derivative (d(Rfu)/dT) to extract the exact transition inflection point.

Example 3: Stabilizing Effect of Six Compatible Solutes of Example 1 on Porcine Insulin The ability of galactosyl lactate 143, galactosyl butyrate 149, galactosyl glycerate 146, glucosyl butyrate 148, glucosyl glycolate 144, and glucosyl malate 150 to stabilize porcine insulin was studied using the DSF assay described in Example 2.

Figure 11:
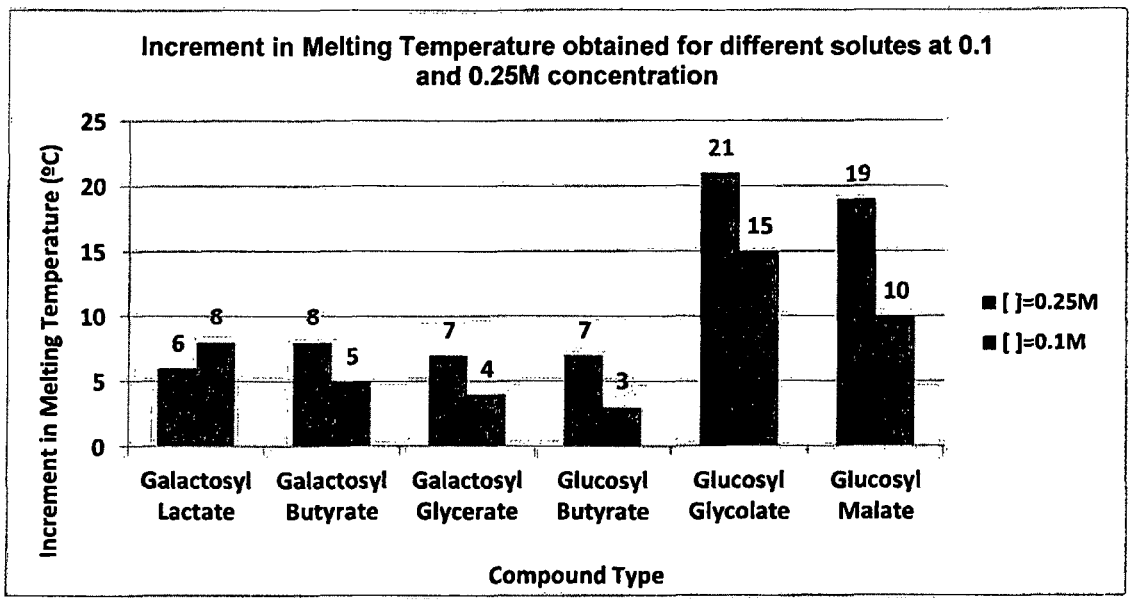
FIG. 11: Increment in melting temperature of porcine insulin obtained for different solutes at 0.1 and 0.25 M. The left bar for each solute shows the result at 0.25 M and the right bar shows the result at 0.1 M.

For the assay, solutions comprising porcine insulin at a concentration of 129 µM and the compatible solutes at concentrations of 0.1 and 0.25 M were made. The increase in melting temperature observed for each solute at 0.1 M and 0.25 M is shown in FIG. 11.

All six solutes stabilized porcine insulin at both concentrations tested, with glucosyl glycolate and glucosyl malate providing the highest increases in melting temperature.

Discussion

The effectiveness of the new compounds in the protection of model proteins against heat-induced inactivation was assessed using DSF, and compared with the effect of natural solutes, like MG and GG as well as potassium chloride, and other previously synthesised non-natural solutes, like MGlyc and ML. DSF proved to be an excellent high-throughput method to obtain rapid information about the stabilising properties of the molecules.

Analysis of the results obtained showed that the stabilisation effect is not general, and strongly depends on specific protein-solute interactions. Although some solutes showed superior thermostabilisation properties, the degree of stabilisation is different for each protein.

The presence of charge is one the most important features for the stabilisation effect. Uncharged solutes, like the glucosamine cyclic derivatives, gave the lowest stabilisation, and malate derivatives, bearing a double charge, were the best stabilisers.

Concerning the use of different hexoses, glucose and galactose derivatives were better stabilisers than the respective mannose and N-acetylglucosamine derivatives. However, the results showed that the group attached to the sugar had more influence for the stabilisation effect than the nature of the sugar.

The results obtained with the α and β anomers of galactosyl glycerates showed that the α derivatives were better stabilisers.

It is expected that the new compounds described herein will stabilize additional proteins as well as other biological materials. Thus, the new compounds of the invention are useful for the stabilization of biological materials used in pharmaceuticals, e.g. biologics such as antibodies and hormones, cosmetics, food products, etc. The compounds of the invention can be used to protect biological materials against temperature stress, aggregation, and high salinity. For example, compounds of the invention can be used to stabilize biologics during processing, e.g. purification, formulation and/or drying, transportation, and storage.

REFERENCES

Costa, M. S. et al., "An overview of the role and diversity of compatible solutes in Bacteria and Archaea," *Biotechnology of Extremophiles*, Antranikian, G., Ed., Springer Berlin Heidelberg: 1998; vol. 61, pp 117-153.

Csiki, Z. and Fugedi, P., "Synthesis of glycosaminoglycan oligosaccharides. Part 4: Synthesis of aza-L-iduronic acid-containing analogs of heparan sulfate oligosaccharides as heparanase inhibitors." *Tetrahedron* 2010, 66, 7821-7837.

Empadinhas, N. et al., "Organic solutes in *Rubrobacter xylanophilus*: the first example of di-myo-inositol-phosphate in a thermophile." *Extremophiles* 2007, 11, 667-673.

Faria, C. et al., "Design of new enzyme stabilizers inspired by glycosides of hyperthermophilic microorganisms," *Carbohydrate Research* 343 (2008) 3025-3033.

Faria, C. et al., "Inhibition of formation of α-synuclein inclusions by mannosylglycerate in a yeast model of Parkinson's disease," *Biochimica et Biophysica Acta* 1830 (2013) 4065-4072.

Goddard-Borger, E. D. et al., "An efficient, inexpensive, and shelf-stable diazotransfer reagent: Imidazole-1-sulfonyl azide hydrochloride," *Organic Letters* 2007, 9, 3797-3800.

Hanessian, S., Preparative Carbohydrate Chemistry. Taylor & Francis: 1997.

Lentzen, G. and Schwarz, T., "Extremolytes: natural compounds from extremophiles for versatile applications," *Appl Microbiol Biotechnol* (2006) 72:623-634.

Lok, C. M et al., "Synthesis of Chiral Glycerides Starting from D-Serine and L-Serine." *Chemistry and Physics of Lipids* 1976, 16, 115-122.

Lourenco, E. C, "Synthesis of potassium (2R)-2-O-alpha-D-glucopyranosyl-(1→6)-alpha-D-glucopyranosyl-2,3-dihydroxypropanoate a natural compatible solute." *Carbohydrate Research* 2009, 344, 2073-2078.

Luley-Goedl, C. and Nidetzky B, "Glycosides as compatible solutes: biosynthesis and applications," *Nat. Prod. Rep.*, (2011), 28, 875-896.

Pais, T. M. et al., "Structural determinants of protein stabilization by solutes—The importance of the hairpin loop in rubredoxins. *Febs Journal* 2005, 272, 999-1011.

PCT International Application Publication No. WO/2007/097653, published Aug. 30, 2007 (Pereira de Oliveira da Silva Santos et al.).

Sharma, S. V. et al., "Chemical and chemoenzymatic syntheses of Bacillithiol: A unique low-molecular-weight thiol amongst low G+C gram-positive bacteria," *Angewandte Chemie—International Edition* 2011, 50, 7101-7104.

What is claimed is:

1. A method of stabilizing a polypeptide, comprising adding to a solution containing the polypeptide at least one compound of the following formula (a) or (b) or a salt thereof, (a)

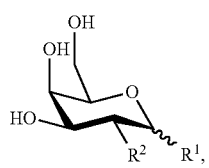

R¹ is —OC(H)(X)(CH₂)ₙC(=O)OH;
R² is —OH;
X is —H, —CH₃ or CH₂C(=O)OH; and
n is 0 or 1;

(b)

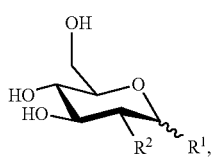

wherein
R¹ is —OC(H)(X)(CH₂)ₙC(=O)OH;
R² is —OH;
X is —H, —CH₃, or CH₂C(=O)OH; and
n is 0 or 1,
so as to thereby stabilize the solution of the polypeptide against heat, wherein the stabilization of the polypeptide is measured by an increase in melting temperature of more than 9° C.

2. The method of claim 1, wherein the compound is (a)

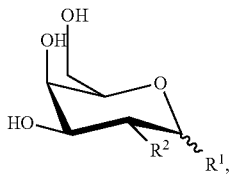

or a salt thereof.

3. The method of claim 2, wherein R¹ is

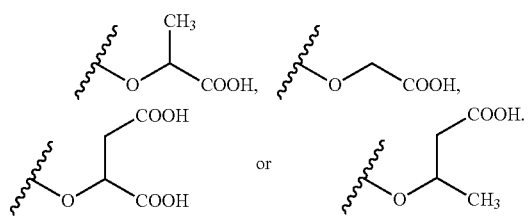

4. The method of claim 2, wherein R¹ is

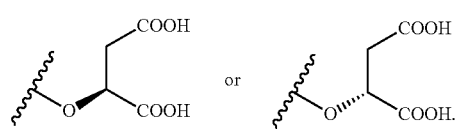 [SMILES: *O[C@@H](CC(=O)O)C(=O)O ; *O[C@H](CC(=O)O)C(=O)O]

5. The method of claim 1, wherein the compound is (b)

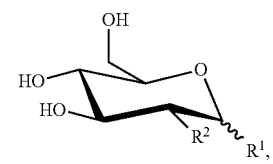

or a salt thereof.

6. The method of claim 5, wherein R₁ is

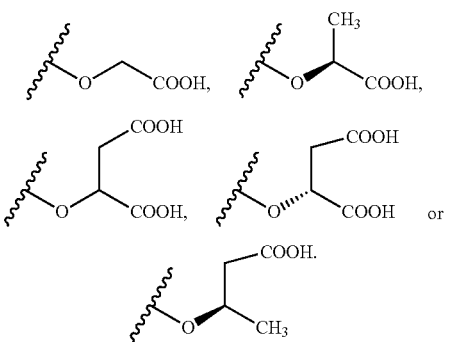

7. The method of claim 5, wherein R₁ is

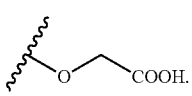

8. The method of claim 5, wherein R₁ is

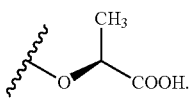 [SMILES: *O[C@@H](C)C(=O)O]

9. The method of claim 5, wherein R₁ is

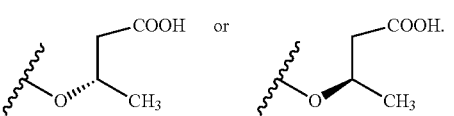

10. The method of claim 5, wherein R¹ is

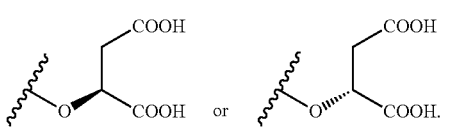 [SMILES: *O[C@@H](CC(=O)O)C(=O)O ; *O[C@H](CC(=O)O)C(=O)O]

11. The method of claim 2, wherein the compound is

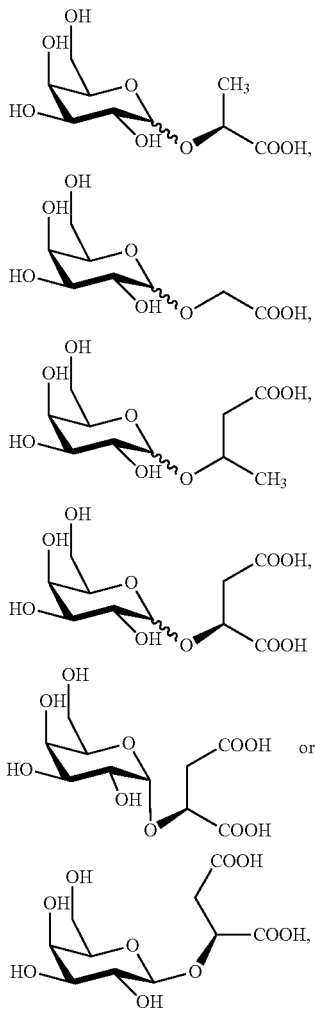

or a salt thereof.

12. The method of claim 5, wherein the compound is

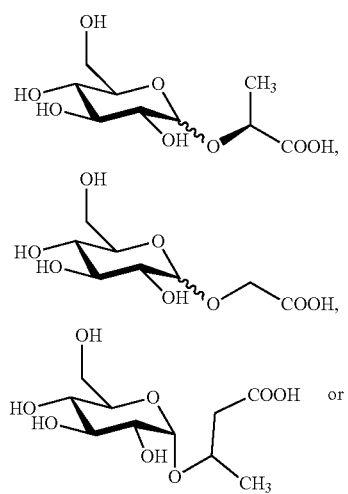

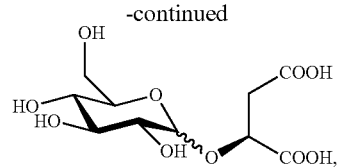

or a salt thereof.

13. The method of claim 1, wherein the α/β anomer ratio of the compound is 1:1 to 99:1.

14. The method of claim 1, wherein the α/β anomer ratio of the compound is greater than 99:1.

15. The method of claim 1, wherein the polypeptide is an enzyme, an antibody, a plasma protein, a hormone, insulin, malate dehydrogenase, staphylococcal nuclease or lysozyme.

16. The method of claim 15, wherein the compound is

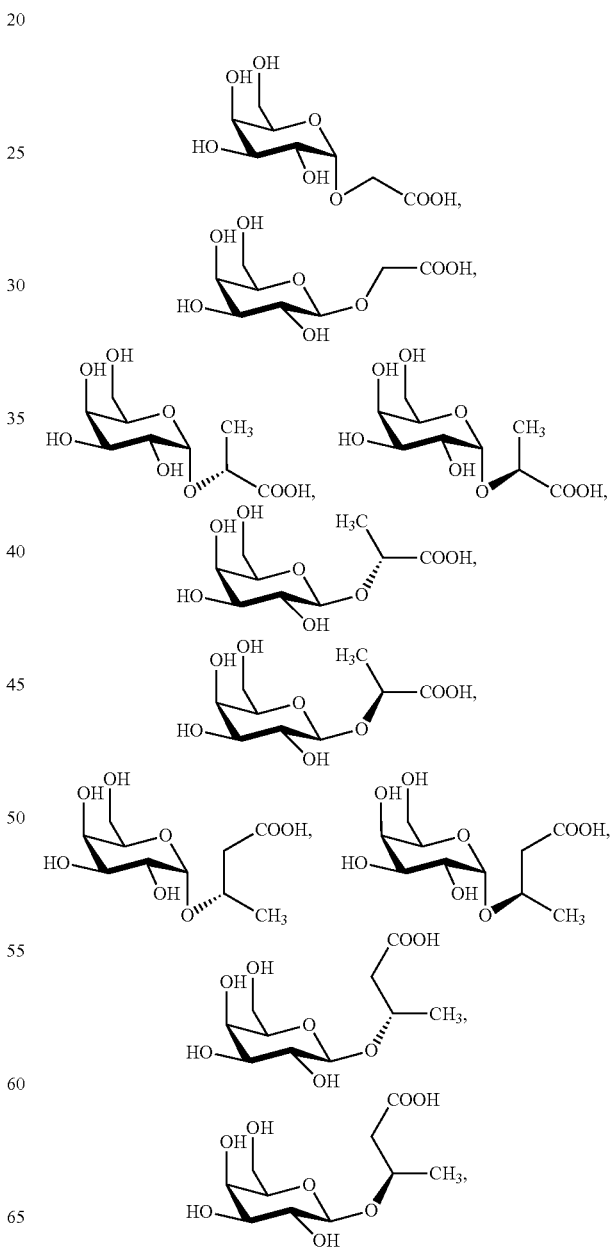

53
-continued
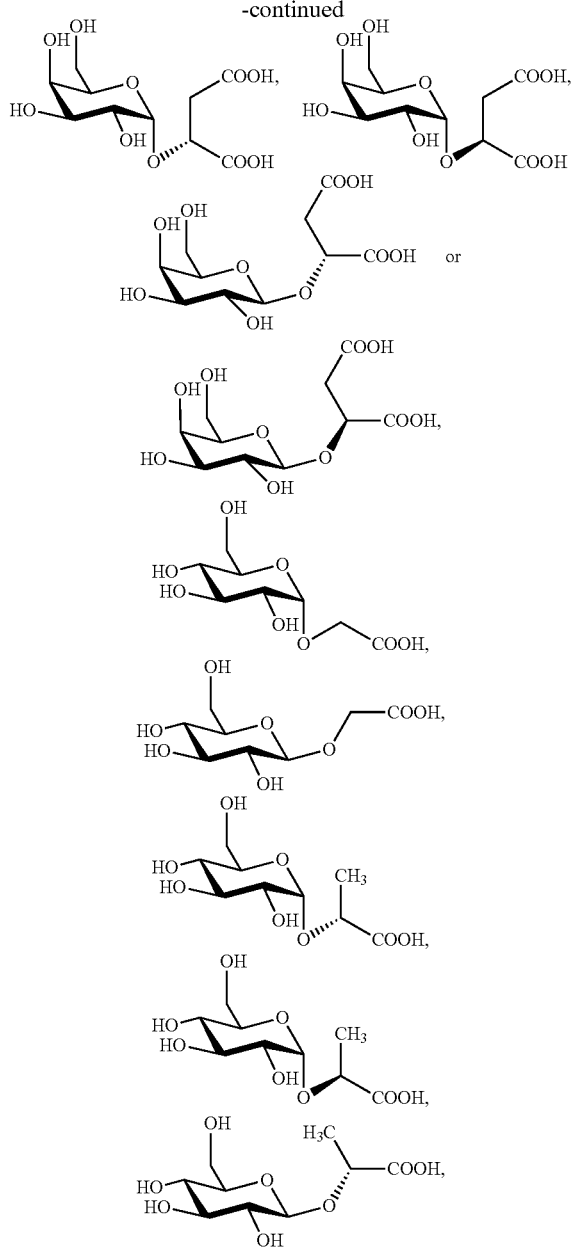
or
54
-continued
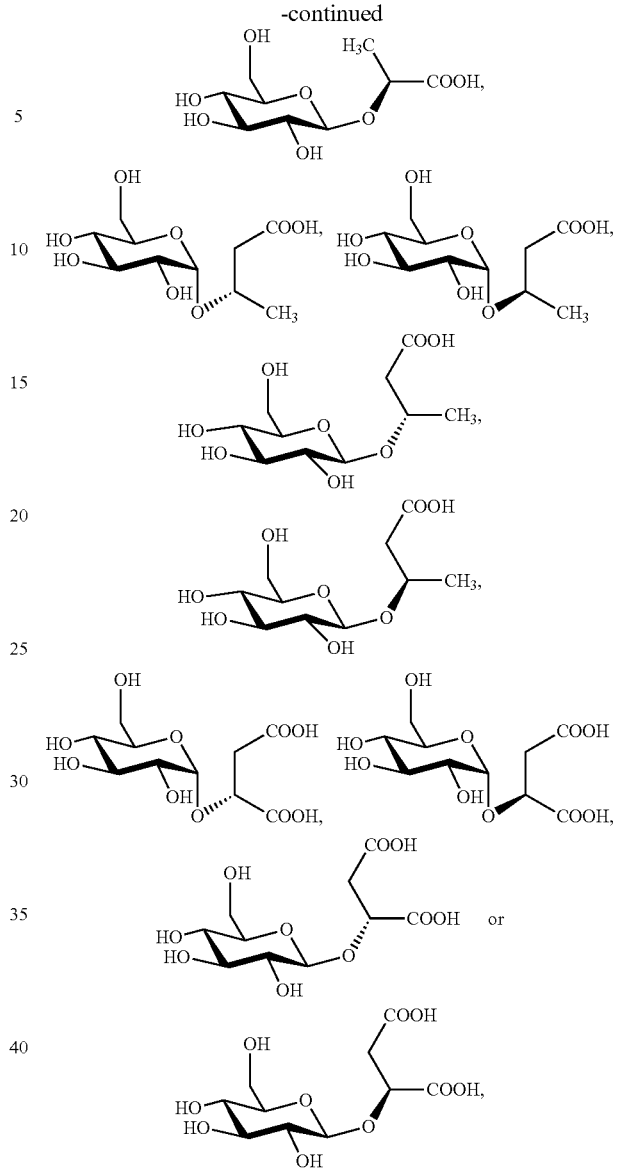
or a salt thereof.
* * * * *